US008515515B2

(12) United States Patent
McKenna et al.

(10) Patent No.: US 8,515,515 B2
(45) Date of Patent: Aug. 20, 2013

(54) MEDICAL SENSOR WITH COMPRESSIBLE LIGHT BARRIER AND TECHNIQUE FOR USING THE SAME

(75) Inventors: Edward M. McKenna, Boulder, CO (US); David Besko, Thornton, CO (US)

(73) Assignee: Covidien LP, Mansfield, MA (US)

( * ) Notice: Subject to any disclaimer, the term of this patent is extended or adjusted under 35 U.S.C. 154(b) by 673 days.

(21) Appl. No.: 12/722,279

(22) Filed: Mar. 11, 2010

(65) Prior Publication Data
US 2010/0249554 A1 Sep. 30, 2010

Related U.S. Application Data

(60) Provisional application No. 61/163,358, filed on Mar. 25, 2009.

(51) Int. Cl.
*A61B 5/1455* (2006.01)
(52) U.S. Cl.
USPC ............................. 600/344; 600/310; 600/323
(58) Field of Classification Search
USPC .................................................. 600/309–344
See application file for complete search history.

(56) References Cited

U.S. PATENT DOCUMENTS

| | | | |
|---|---|---|---|
| 4,025,733 A | 5/1977 | Klar et al. | |
| 4,047,400 A | 9/1977 | Thorneburg | |
| 4,462,116 A | 7/1984 | Sanzone et al. | |
| 4,499,741 A | 2/1985 | Harris | |
| 4,510,938 A | 4/1985 | Jobsis et al. | |
| 4,570,638 A | 2/1986 | Stoddart et al. | |
| 4,675,919 A | 6/1987 | Heine et al. | |
| 4,739,757 A | 4/1988 | Edwards | |
| 4,775,116 A | 10/1988 | Klein | |
| 4,784,162 A | 11/1988 | Ricks et al. | |
| 4,802,485 A | 2/1989 | Bowers et al. | |
| 4,825,872 A | 5/1989 | Tan et al. | |
| 4,825,879 A | 5/1989 | Tan et al. | |
| 4,833,734 A | 5/1989 | Der Estephanian | |
| 4,838,279 A | 6/1989 | Fore | |
| 4,856,116 A | 8/1989 | Sullivan | |
| 4,890,619 A | 1/1990 | Hatschek | |
| 4,910,804 A | 3/1990 | Lidgren | |
| 4,918,758 A | 4/1990 | Rendina | |
| 4,930,888 A | 6/1990 | Freisleben et al. | |
| 4,942,877 A | 7/1990 | Sakai et al. | |

(Continued)

FOREIGN PATENT DOCUMENTS

| | | |
|---|---|---|
| CN | 1306260 | 8/2001 |
| CN | 1657007 | 8/2005 |

(Continued)

OTHER PUBLICATIONS

Soto, Denise A.; "A Comparative Study of Pulse Oximeter Measurements: Digit Versus Earlobe," Master of Science Thesis, California State University Dominguez Hills, May 1997, 46 pgs.

(Continued)

*Primary Examiner* — Eric Winakur
*Assistant Examiner* — Marjan Fardanesh
(74) *Attorney, Agent, or Firm* — Fletcher Yoder, P.C.

(57) ABSTRACT

According to various embodiments, a medical sensor assembly may include compressible light barriers configured to prevent undesired light from being detected. The compressible light barriers may protrude from the surface of the sensor. However, when applied to the tissue, the compressible light barriers may be compressed to the point of being substantially flush with the tissue.

24 Claims, 5 Drawing Sheets

(56) References Cited

U.S. PATENT DOCUMENTS

| | | |
|---|---|---|
| 4,972,331 A | 11/1990 | Chance |
| 4,977,011 A | 12/1990 | Smith |
| 4,991,234 A | 2/1991 | Greenberg |
| 4,996,975 A | 3/1991 | Nakamura |
| 5,005,374 A | 4/1991 | Spitler et al. |
| 5,054,488 A | 10/1991 | Muz |
| 5,080,096 A | 1/1992 | Hooper et al. |
| 5,080,098 A | 1/1992 | Willett et al. |
| H1039 H | 4/1992 | Tripp, Jr. et al. |
| 5,111,817 A | 5/1992 | Clark et al. |
| 5,119,815 A | 6/1992 | Chance |
| 5,122,974 A | 6/1992 | Chance |
| 5,125,403 A | 6/1992 | Culp |
| 5,167,230 A | 12/1992 | Chance |
| 5,188,108 A | 2/1993 | Secker |
| 5,191,891 A | 3/1993 | Righter |
| 5,209,230 A | 5/1993 | Swedlow et al. |
| 5,214,409 A | 5/1993 | Beigel |
| 5,217,012 A | 6/1993 | Young et al. |
| 5,217,013 A | 6/1993 | Lewis et al. |
| 5,241,300 A | 8/1993 | Buschmann |
| 5,246,003 A | 9/1993 | DeLonzor |
| 5,253,645 A | 10/1993 | Friedman et al. |
| 5,267,563 A | 12/1993 | Swedlow et al. |
| 5,267,567 A | 12/1993 | Aung et al. |
| 5,295,490 A | 3/1994 | Dodakian |
| 5,313,940 A | 5/1994 | Fuse et al. |
| 5,337,744 A | 8/1994 | Brianigan |
| 5,348,008 A | 9/1994 | Bornn et al. |
| 5,353,798 A | 10/1994 | Sieben |
| 5,354,979 A | 10/1994 | Adelson et al. |
| 5,357,953 A | 10/1994 | Merrick et al. |
| 5,368,025 A | 11/1994 | Young et al. |
| 5,368,562 A | 11/1994 | Blomquist et al. |
| 5,383,874 A | 1/1995 | Jackson et al. |
| 5,392,777 A | 2/1995 | Swedlow et al. |
| 5,398,689 A | 3/1995 | Conner et al. |
| 5,400,267 A | 3/1995 | Denen et al. |
| 5,405,269 A | 4/1995 | Stupecky |
| 5,405,614 A | 4/1995 | D'Angelo et al. |
| 5,413,099 A | 5/1995 | Schmidt et al. |
| 5,413,101 A | 5/1995 | Sugiura |
| 5,413,102 A | 5/1995 | Schmidt et al. |
| 5,415,166 A | 5/1995 | Imran |
| 5,425,360 A | 6/1995 | Nelson |
| 5,431,170 A | 7/1995 | Mathews |
| 5,437,275 A | 8/1995 | Amundsen et al. |
| 5,437,634 A | 8/1995 | Amano |
| 5,444,254 A | 8/1995 | Thomson |
| 5,451,763 A | 9/1995 | Pickett et al. |
| 5,452,717 A | 9/1995 | Brianigan et al. |
| 5,465,714 A | 11/1995 | Scheuing |
| 5,469,845 A | 11/1995 | DeLonzor et al. |
| 5,482,034 A | 1/1996 | Lewis et al. |
| 5,490,523 A | 2/1996 | Isaacson et al. |
| 5,528,519 A | 6/1996 | Ohkura et al. |
| 5,546,955 A | 8/1996 | Wilk |
| 5,551,423 A | 9/1996 | Sugiura |
| 5,562,718 A | 10/1996 | Palermo |
| 5,564,108 A | 10/1996 | Hunsaker et al. |
| 5,564,417 A | 10/1996 | Chance |
| 5,584,296 A | 12/1996 | Cui et al. |
| 5,592,408 A | 1/1997 | Keskin et al. |
| 5,596,987 A | 1/1997 | Chance |
| 5,617,865 A | 4/1997 | Palczewska et al. |
| 5,617,866 A | 4/1997 | Marian, Jr. |
| 5,627,323 A | 5/1997 | Stern |
| 5,634,466 A | 6/1997 | Gruner |
| 5,638,593 A | 6/1997 | Gerhardt et al. |
| 5,638,818 A | 6/1997 | Diab et al. |
| 5,640,953 A | 6/1997 | Bishop et al. |
| 5,645,440 A | 7/1997 | Tobler et al. |
| 5,645,586 A | 7/1997 | Meltzer |
| 5,646,416 A | 7/1997 | Van De Velde |
| 5,671,750 A | 9/1997 | Shinoda |
| 5,673,708 A | 10/1997 | Athanasiou et al. |
| 5,678,544 A | 10/1997 | DeLonzor et al. |
| 5,681,285 A | 10/1997 | Ford et al. |
| 5,683,434 A | 11/1997 | Archer |
| 5,697,363 A | 12/1997 | Hart |
| 5,697,367 A | 12/1997 | Lewis et al. |
| 5,701,894 A | 12/1997 | Cherry et al. |
| 5,706,820 A | 1/1998 | Hossack et al. |
| 5,732,475 A | 3/1998 | Sacks et al. |
| 5,738,612 A | 4/1998 | Tsuda |
| 5,743,856 A | 4/1998 | Oka et al. |
| 5,743,857 A | 4/1998 | Shinoda et al. |
| 5,752,913 A | 5/1998 | Oka |
| 5,752,920 A | 5/1998 | Ogura et al. |
| 5,758,644 A | 6/1998 | Diab et al. |
| 5,772,601 A | 6/1998 | Oka et al. |
| 5,776,058 A | 7/1998 | Levinson et al. |
| 5,776,071 A | 7/1998 | Inukai et al. |
| 5,779,631 A | 7/1998 | Chance |
| 5,779,639 A | 7/1998 | Yeung |
| 5,782,757 A | 7/1998 | Diab et al. |
| 5,786,592 A | 7/1998 | Hök |
| 5,791,347 A | 8/1998 | Flaherty et al. |
| 5,791,348 A | 8/1998 | Aung et al. |
| 5,792,052 A | 8/1998 | Isaacson et al. |
| 5,792,058 A | 8/1998 | Lee et al. |
| 5,797,841 A | 8/1998 | Delonzor et al. |
| 5,810,724 A | 9/1998 | Gronvall |
| 5,813,980 A | 9/1998 | Levinson et al. |
| 5,823,012 A | 10/1998 | Hacskaylo |
| 5,823,952 A | 10/1998 | Levinson et al. |
| 5,826,277 A | 10/1998 | McConville |
| 5,830,136 A | 11/1998 | Delonzor et al. |
| 5,830,137 A | 11/1998 | Scharf et al. |
| 5,830,148 A | 11/1998 | Inukai et al. |
| 5,830,149 A | 11/1998 | Oka et al. |
| 5,833,602 A | 11/1998 | Osemwota |
| 5,836,887 A | 11/1998 | Oka et al. |
| 5,839,439 A | 11/1998 | Nierlich et al. |
| RE36,000 E | 12/1998 | Swedlow et al. |
| 5,842,981 A | 12/1998 | Larsen et al. |
| 5,842,982 A | 12/1998 | Mannheimer |
| 5,851,179 A | 12/1998 | Ritson et al. |
| 5,857,974 A | 1/1999 | Eberle et al. |
| 5,860,932 A | 1/1999 | Goto et al. |
| 5,860,957 A | 1/1999 | Jacobsen et al. |
| 5,868,133 A | 2/1999 | DeVries et al. |
| 5,870,626 A | 2/1999 | Lebeau |
| 5,872,713 A | 2/1999 | Douglas et al. |
| 5,873,821 A | 2/1999 | Chance et al. |
| 5,879,294 A | 3/1999 | Anderson et al. |
| 5,891,021 A | 4/1999 | Dillon et al. |
| 5,891,026 A | 4/1999 | Wang et al. |
| 5,895,359 A | 4/1999 | Peel |
| 5,902,235 A | 5/1999 | Lewis et al. |
| 5,906,581 A | 5/1999 | Tsuda |
| 5,913,819 A | 6/1999 | Taylor et al. |
| 5,916,154 A | 6/1999 | Hobbs et al. |
| 5,919,133 A | 7/1999 | Taylor et al. |
| 5,931,790 A | 8/1999 | Peel |
| 5,931,791 A | 8/1999 | Saltzstein et al. |
| 5,934,925 A | 8/1999 | Tobler et al. |
| 5,936,539 A | 8/1999 | Fuchs |
| 5,947,905 A | 9/1999 | Hadjicostis et al. |
| 5,954,053 A | 9/1999 | Chance et al. |
| 5,957,850 A | 9/1999 | Marian, Jr. et al. |
| 5,964,701 A | 10/1999 | Asada et al. |
| 5,980,464 A | 11/1999 | Tsuda |
| 5,983,129 A | 11/1999 | Cowan et al. |
| 5,987,343 A | 11/1999 | Kinast |
| 5,987,351 A | 11/1999 | Chance |
| 5,991,648 A | 11/1999 | Levin |
| 5,995,077 A | 11/1999 | Wilcox et al. |
| 5,995,855 A | 11/1999 | Kiani et al. |
| 5,995,856 A | 11/1999 | Mannheimer et al. |
| 5,995,857 A | 11/1999 | Toomim et al. |
| 6,007,492 A | 12/1999 | Goto et al. |
| 6,011,986 A | 1/2000 | Diab et al. |
| 6,022,320 A | 2/2000 | Ogura et al. |

| Patent | Kind | Date | Inventors |
|---|---|---|---|
| 6,027,453 | A | 2/2000 | Miwa et al. |
| 6,030,351 | A | 2/2000 | Schmidt et al. |
| 6,031,603 | A | 2/2000 | Fine et al. |
| 6,036,651 | A | 3/2000 | Inukai et al. |
| 6,041,247 | A | 3/2000 | Weckstrom et al. |
| 6,047,201 | A | 4/2000 | Jackson |
| 6,047,203 | A | 4/2000 | Sackner et al. |
| 6,049,958 | A | 4/2000 | Eberle et al. |
| 6,050,951 | A | 4/2000 | Friedman et al. |
| 6,052,619 | A | 4/2000 | John |
| 6,073,038 | A | 6/2000 | Wang et al. |
| 6,084,380 | A | 7/2000 | Burton |
| 6,085,752 | A | 7/2000 | Kehr et al. |
| 6,088,607 | A | 7/2000 | Diab et al. |
| 6,106,780 | A | 8/2000 | Douglas et al. |
| 6,112,107 | A | 8/2000 | Hannula |
| 6,115,621 | A | 9/2000 | Chin |
| 6,118,382 | A | 9/2000 | Hibbs et al. |
| 6,134,459 | A | 10/2000 | Roberts et al. |
| 6,144,868 | A | 11/2000 | Parker |
| 6,149,481 | A | 11/2000 | Wang et al. |
| 6,152,754 | A | 11/2000 | Gerhardt et al. |
| 6,154,667 | A | 11/2000 | Miura et al. |
| 6,162,188 | A | 12/2000 | Barnea |
| 6,165,173 | A | 12/2000 | Kamdar et al. |
| 6,171,258 | B1 | 1/2001 | Katakasoglu et al. |
| 6,173,196 | B1 | 1/2001 | Delonzor et al. |
| 6,179,786 | B1 | 1/2001 | Young |
| 6,181,959 | B1 | 1/2001 | Schollermann et al. |
| 6,184,521 | B1 | 2/2001 | Coffin, IV et al. |
| 6,186,953 | B1 | 2/2001 | Narimatsu |
| 6,186,954 | B1 | 2/2001 | Narimatsu |
| 6,190,325 | B1 | 2/2001 | Narimatsu |
| 6,196,974 | B1 | 3/2001 | Miwa |
| 6,198,952 | B1 | 3/2001 | Miesel |
| 6,199,550 | B1 | 3/2001 | Wiesmann et al. |
| 6,209,144 | B1 | 4/2001 | Carter |
| 6,216,021 | B1 | 4/2001 | Franceschini et al. |
| 6,223,063 | B1 | 4/2001 | Chaiken et al. |
| 6,241,680 | B1 | 6/2001 | Miwa |
| 6,248,083 | B1 | 6/2001 | Smith et al. |
| 6,251,076 | B1 | 6/2001 | Hovland et al. |
| 6,251,080 | B1 | 6/2001 | Henkin et al. |
| 6,251,081 | B1 | 6/2001 | Narimatsu |
| 6,251,113 | B1 | 6/2001 | Appelbaum et al. |
| 6,256,523 | B1 | 7/2001 | Diab et al. |
| 6,256,524 | B1 | 7/2001 | Walker et al. |
| 6,263,221 | B1 | 7/2001 | Chance et al. |
| 6,263,223 | B1 | 7/2001 | Shepherd et al. |
| 6,280,213 | B1 | 8/2001 | Tobler et al. |
| 6,282,450 | B1 | 8/2001 | Hartlaub et al. |
| 6,283,922 | B1 | 9/2001 | Goto et al. |
| 6,285,895 | B1 | 9/2001 | Ristolainen et al. |
| 6,306,076 | B1 | 10/2001 | Gill |
| 6,308,089 | B1 | 10/2001 | von der Ruhr et al. |
| 6,321,100 | B1 | 11/2001 | Parker |
| 6,322,516 | B1 | 11/2001 | Masuda et al. |
| 6,343,223 | B1 | 1/2002 | Chin et al. |
| 6,343,224 | B1 | 1/2002 | Parker |
| 6,346,886 | B1 | 2/2002 | De La Huerga |
| 6,349,228 | B1 | 2/2002 | Kiani et al. |
| 6,356,774 | B1 | 3/2002 | Bernstein et al. |
| 6,362,622 | B1 | 3/2002 | Stauber et al. |
| 6,368,282 | B1 | 4/2002 | Oka et al. |
| 6,370,411 | B1 | 4/2002 | Osadchy et al. |
| 6,377,829 | B1 | 4/2002 | Al-Ali |
| 6,381,480 | B1 | 4/2002 | Stoddart et al. |
| 6,381,481 | B1 | 4/2002 | Levendowski et al. |
| 6,385,486 | B1 | 5/2002 | John et al. |
| 6,385,821 | B1 | 5/2002 | Modgil et al. |
| 6,387,092 | B1 | 5/2002 | Burnside et al. |
| 6,388,240 | B2 | 5/2002 | Schulz et al. |
| 6,397,091 | B2 | 5/2002 | Diab et al. |
| 6,405,075 | B1 | 6/2002 | Levin |
| 6,416,471 | B1 | 7/2002 | Kumar et al. |
| 6,416,474 | B1 | 7/2002 | Penner et al. |
| 6,417,774 | B1 | 7/2002 | Hibbs et al. |
| 6,423,010 | B1 | 7/2002 | Friedman et al. |
| 6,430,423 | B2 | 8/2002 | DeLonzor et al. |
| 6,432,050 | B1 | 8/2002 | Porat et al. |
| 6,450,168 | B1 | 9/2002 | Nguyen |
| 6,450,957 | B1 | 9/2002 | Yoshimi et al. |
| 6,450,981 | B1 | 9/2002 | Shabty et al. |
| 6,454,708 | B1 | 9/2002 | Ferguson et al. |
| 6,461,305 | B1 | 10/2002 | Schnall |
| 6,463,310 | B1 | 10/2002 | Swedlow et al. |
| 6,466,809 | B1 | 10/2002 | Riley |
| 6,468,241 | B1 | 10/2002 | Gelfand et al. |
| 6,470,199 | B1 | 10/2002 | Kopotic et al. |
| 6,470,279 | B1 | 10/2002 | Samsoondar |
| 6,480,762 | B1 | 11/2002 | Uchikubo et al. |
| 6,491,638 | B2 | 12/2002 | Oka |
| 6,491,639 | B1 | 12/2002 | Turcott |
| 6,503,087 | B1 | 1/2003 | Eggert et al. |
| 6,503,204 | B1 | 1/2003 | Sumanaweera et al. |
| 6,505,061 | B2 | 1/2003 | Larson |
| 6,511,478 | B1 | 1/2003 | Burnside et al. |
| 6,516,289 | B2 | 2/2003 | David |
| 6,519,487 | B1 | 2/2003 | Parker |
| 6,524,257 | B2 | 2/2003 | Ogura |
| 6,525,386 | B1 | 2/2003 | Mills et al. |
| 6,526,309 | B1 | 2/2003 | Chance |
| 6,526,970 | B2 | 3/2003 | DeVries et al. |
| 6,527,725 | B1 | 3/2003 | Inukai et al. |
| 6,527,726 | B2 | 3/2003 | Goto et al. |
| 6,535,765 | B1 | 3/2003 | Amely-Velez et al. |
| 6,537,220 | B1 | 3/2003 | Friemel et al. |
| 6,541,756 | B2 | 4/2003 | Schulz et al. |
| 6,542,081 | B2 | 4/2003 | Torch |
| 6,547,742 | B2 | 4/2003 | Oka et al. |
| 6,547,743 | B2 | 4/2003 | Brydon |
| 6,551,252 | B2 | 4/2003 | Sackner et al. |
| 6,553,242 | B1 | 4/2003 | Sarussi |
| 6,575,902 | B1 | 6/2003 | Burton |
| 6,575,904 | B2 | 6/2003 | Nagai et al. |
| 6,580,086 | B1 | 6/2003 | Schulz et al. |
| 6,582,371 | B2 | 6/2003 | Miller |
| 6,582,374 | B2 | 6/2003 | Yokozeki |
| 6,584,356 | B2 | 6/2003 | Wassmund et al. |
| 6,589,171 | B2 | 7/2003 | Keirsbilck |
| 6,589,183 | B2 | 7/2003 | Yokozeki |
| 6,589,189 | B2 | 7/2003 | Meyerson et al. |
| 6,594,513 | B1 | 7/2003 | Jobsis et al. |
| 6,597,933 | B2 | 7/2003 | Kiani et al. |
| 6,605,038 | B1 | 8/2003 | Teller et al. |
| 6,606,993 | B1 | 8/2003 | Wiesmann et al. |
| 6,611,793 | B1 | 8/2003 | Burnside et al. |
| 6,615,065 | B1 | 9/2003 | Barrett et al. |
| 6,622,034 | B1 | 9/2003 | Gorski et al. |
| 6,635,048 | B1 | 10/2003 | Ullestad et al. |
| 6,640,116 | B2 | 10/2003 | Diab |
| 6,645,154 | B2 | 11/2003 | Oka |
| 6,645,155 | B2 | 11/2003 | Inukai et al. |
| 6,653,557 | B2 | 11/2003 | Wolf et al. |
| 6,654,622 | B1 | 11/2003 | Eberhard et al. |
| 6,662,033 | B2 | 12/2003 | Casciani et al. |
| 6,666,860 | B1 | 12/2003 | Takahashi |
| 6,671,531 | B2 | 12/2003 | Al-Ali et al. |
| 6,671,545 | B2 | 12/2003 | Fincke |
| 6,678,543 | B2 | 1/2004 | Diab et al. |
| 6,681,454 | B2 | 1/2004 | Modgil et al. |
| 6,684,091 | B2 | 1/2004 | Parker |
| 6,694,155 | B1 | 2/2004 | Chin |
| 6,695,806 | B2 | 2/2004 | Gelfand et al. |
| 6,700,497 | B2 | 3/2004 | Hibbs et al. |
| 6,704,601 | B1 | 3/2004 | Amely-Velez et al. |
| 6,708,048 | B1 | 3/2004 | Chance |
| 6,711,425 | B1 | 3/2004 | Reuss |
| 6,712,767 | B2 | 3/2004 | Hossack et al. |
| 6,721,585 | B1 | 4/2004 | Parker |
| 6,721,602 | B2 | 4/2004 | Engmark et al. |
| 6,725,075 | B2 | 4/2004 | Al-Ali |
| 6,726,327 | B2 | 4/2004 | Torrey et al. |
| 6,731,963 | B2 | 5/2004 | Finarov et al. |
| 6,735,459 | B2 | 5/2004 | Parker |
| 6,736,759 | B1 | 5/2004 | Stubbs et al. |
| 6,736,786 | B1 | 5/2004 | Shabty et al. |
| 6,743,173 | B2 | 6/2004 | Penner et al. |

| Patent No. | Date | Inventor |
|---|---|---|
| 6,743,202 B2 | 6/2004 | Hirschman et al. |
| 6,745,061 B1 | 6/2004 | Hicks et al. |
| 6,748,254 B2 | 6/2004 | O'Neil et al. |
| 6,748,262 B2 | 6/2004 | Harada et al. |
| 6,749,567 B2 | 6/2004 | Davis |
| 6,755,789 B2 | 6/2004 | Stringer et al. |
| 6,758,808 B2 | 7/2004 | Paul |
| 6,763,255 B2 | 7/2004 | Delonzor et al. |
| 6,767,330 B2 | 7/2004 | Lavery |
| 6,771,994 B2 | 8/2004 | Kiani et al. |
| 6,776,758 B2 | 8/2004 | Peszynski et al. |
| 6,779,257 B2 | 8/2004 | Kiepen et al. |
| 6,785,568 B2 | 8/2004 | Chance |
| 6,792,300 B1 | 9/2004 | Diab et al. |
| 6,796,946 B2 | 9/2004 | Ogura et al. |
| 6,801,799 B2 | 10/2004 | Mendelson |
| 6,804,543 B2 | 10/2004 | Miller et al. |
| 6,804,558 B2 | 10/2004 | Haller et al. |
| 6,808,496 B2 | 10/2004 | Oka et al. |
| 6,811,538 B2 | 11/2004 | Westbrook et al. |
| 6,813,511 B2 | 11/2004 | Diab et al. |
| 6,824,520 B2 | 11/2004 | Orr et al. |
| 6,827,688 B2 | 12/2004 | Goto et al. |
| 6,829,003 B2 | 12/2004 | Takami |
| 6,830,711 B2 | 12/2004 | Mills et al. |
| 6,832,987 B2 | 12/2004 | David et al. |
| 6,842,722 B2 | 1/2005 | David |
| 6,847,294 B1 | 1/2005 | Lin et al. |
| 6,849,074 B2 | 2/2005 | Chen et al. |
| 6,853,304 B2 | 2/2005 | Reisman et al. |
| 6,870,479 B2 | 3/2005 | Gabriel |
| 6,875,176 B2 | 4/2005 | Mourad et al. |
| 6,877,511 B2 | 4/2005 | DeVries et al. |
| 6,893,400 B2 | 5/2005 | Kawaguchi et al. |
| 6,898,299 B1 | 5/2005 | Brooks |
| 6,899,682 B2 | 5/2005 | Eberle et al. |
| 6,899,684 B2 | 5/2005 | Mault et al. |
| 6,904,124 B2 | 6/2005 | Staver et al. |
| 6,907,284 B2 | 6/2005 | Hamilton et al. |
| 6,909,912 B2 | 6/2005 | Melker |
| 6,911,027 B1 | 6/2005 | Edwards et al. |
| 6,915,167 B2 | 7/2005 | Splett et al. |
| 6,920,345 B2 | 7/2005 | Al-Ali et al. |
| 6,921,198 B2 | 7/2005 | Gruszecki et al. |
| 6,923,771 B2 | 8/2005 | Ogura et al. |
| 6,923,776 B2 | 8/2005 | Shabty et al. |
| 6,930,608 B2 | 8/2005 | Grajales et al. |
| 6,934,570 B2 | 8/2005 | Kiani et al. |
| 6,934,571 B2 | 8/2005 | Weismann et al. |
| 6,936,011 B2 | 8/2005 | Sheldon |
| 6,938,488 B2 | 9/2005 | Diaz et al. |
| 6,939,314 B2 | 9/2005 | Hall et al. |
| 6,943,881 B2 | 9/2005 | Wang |
| 6,944,498 B2 | 9/2005 | Owens et al. |
| 6,952,870 B2 | 10/2005 | Miller |
| 6,955,650 B2 | 10/2005 | Mault et al. |
| 6,965,071 B2 | 11/2005 | Watchko et al. |
| 6,971,790 B2 | 12/2005 | Quinn et al. |
| 6,979,329 B2 | 12/2005 | Burnside et al. |
| 6,985,763 B2 | 1/2006 | Boas et al. |
| 6,985,764 B2 | 1/2006 | Mason et al. |
| 6,990,371 B2 | 1/2006 | Powers et al. |
| 6,993,371 B2 | 1/2006 | Kiani et al. |
| 6,995,665 B2 | 2/2006 | Appelt et al. |
| 7,001,334 B2 | 2/2006 | Reed et al. |
| 7,017,420 B2 | 3/2006 | Kalvesten et al. |
| 7,018,338 B2 | 3/2006 | Vetter et al. |
| 7,019,392 B2 | 3/2006 | Iwasaki |
| 7,020,508 B2 | 3/2006 | Stivoric et al. |
| 7,024,235 B2 | 4/2006 | Melker et al. |
| 7,027,850 B2 | 4/2006 | Wasserman |
| 7,027,871 B2 | 4/2006 | Burnes et al. |
| 7,033,316 B2 | 4/2006 | Takahashi |
| 7,039,449 B2 | 5/2006 | Al-Ali |
| 7,041,121 B1 | 5/2006 | Williams et al. |
| 7,047,054 B2 | 5/2006 | Benni |
| 7,047,055 B2 | 5/2006 | Boas et al. |
| 7,048,687 B1 | 5/2006 | Reuss et al. |
| 7,052,509 B2 | 5/2006 | Lennox |
| 7,054,453 B2 | 5/2006 | Causevic et al. |
| 7,054,454 B2 | 5/2006 | Causevic et al. |
| 7,063,669 B2 | 6/2006 | Brawner et al. |
| 7,067,893 B2 | 6/2006 | Mills et al. |
| 7,072,704 B2 | 7/2006 | Bucholz |
| 7,079,036 B2 | 7/2006 | Cooper et al. |
| 7,081,128 B2 | 7/2006 | Hart et al. |
| 7,085,597 B2 | 8/2006 | Fein et al. |
| 7,087,023 B2 | 8/2006 | Daft et al. |
| 7,089,061 B2 | 8/2006 | Grey |
| 7,096,052 B2 | 8/2006 | Mason et al. |
| 7,096,054 B2 | 8/2006 | Abdul-Hafiz et al. |
| 7,097,621 B2 | 8/2006 | Narimatsu et al. |
| 7,107,706 B1 | 9/2006 | Bailey |
| 7,108,659 B2 | 9/2006 | Ross |
| 7,112,196 B2 | 9/2006 | Brosch et al. |
| 7,113,815 B2 | 9/2006 | O'Neil et al. |
| RE39,359 E | 10/2006 | McGraw et al. |
| 7,122,005 B2 | 10/2006 | Shusterman |
| 7,125,383 B2 | 10/2006 | Hoctor et al. |
| 7,127,278 B2 | 10/2006 | Melker et al. |
| 7,132,641 B2 | 11/2006 | Schulz et al. |
| 7,136,452 B2 | 11/2006 | Spartiotis et al. |
| 7,143,305 B2 | 11/2006 | Hajjai et al. |
| 7,158,822 B2 | 1/2007 | Payne, Jr. |
| 7,160,284 B2 | 1/2007 | Ullestad et al. |
| 7,161,484 B2 | 1/2007 | Tsoukalis |
| 7,164,938 B2 | 1/2007 | Geddes et al. |
| 7,167,743 B2 | 1/2007 | Heruth et al. |
| 7,171,251 B2 | 1/2007 | Sarussi et al. |
| 7,179,228 B2 | 2/2007 | Banet |
| 7,181,264 B2 | 2/2007 | Wiesmann et al. |
| 7,181,505 B2 | 2/2007 | Haller et al. |
| 7,190,987 B2 | 3/2007 | Lindekugel |
| 7,192,403 B2 | 3/2007 | Russell et al. |
| 7,197,357 B2 | 3/2007 | Istvan et al. |
| 7,198,605 B2 | 4/2007 | Donofrio et al. |
| 7,204,250 B1 | 4/2007 | Burton |
| 7,214,191 B2 | 5/2007 | Stringer et al. |
| 7,218,232 B2 | 5/2007 | DiSilvestro et al. |
| 7,220,220 B2 | 5/2007 | Stubbs et al. |
| 7,222,624 B2 | 5/2007 | Rashad |
| 7,224,282 B2 | 5/2007 | Terauchi et al. |
| 7,225,007 B2 | 5/2007 | Al-Ali et al. |
| 7,229,400 B2 | 6/2007 | Elliott et al. |
| 7,245,953 B1 | 7/2007 | Parker |
| 7,248,905 B2 | 7/2007 | Fukuda et al. |
| 7,248,910 B2 | 7/2007 | Li et al. |
| 7,254,444 B2 | 8/2007 | Moore et al. |
| 7,255,475 B2 | 8/2007 | Quinn et al. |
| 7,257,448 B2 | 8/2007 | Crowe et al. |
| 7,263,393 B2 | 8/2007 | Smith et al. |
| 7,270,636 B2 | 9/2007 | Lin et al. |
| 7,280,858 B2 | 10/2007 | Al-Ali et al. |
| 7,297,119 B2 | 11/2007 | Westbrook et al. |
| 7,303,680 B2 | 12/2007 | Connell et al. |
| 7,313,427 B2 | 12/2007 | Benni |
| 7,349,726 B2 | 3/2008 | Casciani et al. |
| 7,376,454 B2 | 5/2008 | Casciani et al. |
| 7,398,115 B2 | 7/2008 | Lynn |
| 7,415,298 B2 | 8/2008 | Casciani et al. |
| 2001/0000790 A1 | 5/2001 | DeLonzor et al. |
| 2001/0009398 A1 | 7/2001 | Sekura et al. |
| 2002/0013538 A1 | 1/2002 | Teller |
| 2002/0042558 A1 | 4/2002 | Mendelson |
| 2002/0052539 A1 | 5/2002 | Haller et al. |
| 2002/0084904 A1 | 7/2002 | De La Huerga |
| 2002/0091335 A1 | 7/2002 | John et al. |
| 2002/0095092 A1 | 7/2002 | Kondo et al. |
| 2002/0103445 A1 | 8/2002 | Rahdert et al. |
| 2002/0109600 A1 | 8/2002 | Mault et al. |
| 2002/0124295 A1 | 9/2002 | Fenwick et al. |
| 2002/0139368 A1 | 10/2002 | Bachinski |
| 2002/0148470 A1 | 10/2002 | Blue et al. |
| 2002/0151929 A1 | 10/2002 | Goto et al. |
| 2002/0156354 A1 | 10/2002 | Larson |
| 2002/0161290 A1 | 10/2002 | Chance |
| 2002/0161309 A1 | 10/2002 | Marro |
| 2002/0173706 A1 | 11/2002 | Takatani et al. |

| | | | | | | |
|---|---|---|---|---|---|---|
| 2002/0173708 A1 | 11/2002 | DeLonzor et al. | | 2005/0222502 A1 | 10/2005 | Cooper |
| 2003/0004547 A1 | 1/2003 | Owens et al. | | 2005/0222522 A1 | 10/2005 | Heruth et al. |
| 2003/0009119 A1 | 1/2003 | Kamm et al. | | 2005/0228234 A1 | 10/2005 | Yang |
| 2003/0009308 A1 | 1/2003 | Kirtley | | 2005/0228297 A1 | 10/2005 | Banet et al. |
| 2003/0018243 A1 | 1/2003 | Gerhardt et al. | | 2005/0228299 A1 | 10/2005 | Banet et al. |
| 2003/0023140 A1 | 1/2003 | Chance | | 2005/0231686 A1 | 10/2005 | Rathjen |
| 2003/0036685 A1 | 2/2003 | Goodman | | 2005/0234312 A1 | 10/2005 | Suzuki et al. |
| 2003/0065275 A1 | 4/2003 | Mault et al. | | 2005/0234317 A1 | 10/2005 | Kiani |
| 2003/0086156 A1 | 5/2003 | McGuire | | 2005/0234518 A1 | 10/2005 | Heruth et al. |
| 2003/0120183 A1 | 6/2003 | Simmons | | 2005/0240087 A1 | 10/2005 | Keenan et al. |
| 2003/0122706 A1 | 7/2003 | Choi et al. | | 2005/0256523 A1 | 11/2005 | Chen et al. |
| 2003/0125616 A1 | 7/2003 | Black et al. | | 2005/0261594 A1 | 11/2005 | Banet |
| 2003/0135127 A1 | 7/2003 | Sackner et al. | | 2005/0268916 A1 | 12/2005 | Mumford et al. |
| 2003/0144579 A1 | 7/2003 | Buss | | 2005/0277819 A1 | 12/2005 | Kiani et al. |
| 2003/0156288 A1 | 8/2003 | Barnum et al. | | 2005/0283082 A1 | 12/2005 | Geddes et al. |
| 2003/0176810 A1 | 9/2003 | Maahs et al. | | 2006/0009685 A1 | 1/2006 | Finarov et al. |
| 2003/0189492 A1 | 10/2003 | Harvie | | 2006/0009698 A1 | 1/2006 | Banet et al. |
| 2003/0216728 A1 | 11/2003 | Stern et al. | | 2006/0020181 A1 | 1/2006 | Schmitt |
| 2003/0225323 A1 | 12/2003 | Kiani et al. | | 2006/0030049 A1 | 2/2006 | Bhimani et al. |
| 2004/0002655 A1 | 1/2004 | Bolorforosh et al. | | 2006/0030767 A1 | 2/2006 | Lang et al. |
| 2004/0007585 A1 | 1/2004 | Griffith et al. | | 2006/0036179 A1 | 2/2006 | Miller |
| 2004/0030258 A1 | 2/2004 | Williams et al. | | 2006/0047447 A1 | 3/2006 | Brady et al. |
| 2004/0044545 A1 | 3/2004 | Wiesmann et al. | | 2006/0058593 A1 | 3/2006 | Drinan et al. |
| 2004/0054287 A1 | 3/2004 | Stephens | | 2006/0058690 A1 | 3/2006 | Bartnik et al. |
| 2004/0054291 A1 | 3/2004 | Schulz et al. | | 2006/0064133 A1 | 3/2006 | Von Arx et al. |
| 2004/0064097 A1 | 4/2004 | Peterson | | 2006/0064134 A1 | 3/2006 | Mazar et al. |
| 2004/0064165 A1 | 4/2004 | Thompson | | 2006/0064142 A1 | 3/2006 | Chavan et al. |
| 2004/0082842 A1 | 4/2004 | Lumba et al. | | 2006/0064143 A1 | 3/2006 | Von Arx et al. |
| 2004/0092919 A1 | 5/2004 | Ritchie et al. | | 2006/0074283 A1 | 4/2006 | Henderson et al. |
| 2004/0100784 A1 | 5/2004 | Willers et al. | | 2006/0074324 A1 | 4/2006 | Wu et al. |
| 2004/0102931 A1 | 5/2004 | Ellis et al. | | 2006/0084848 A1 | 4/2006 | Mitchnick |
| 2004/0117891 A1 | 6/2004 | Hannula et al. | | 2006/0084852 A1 | 4/2006 | Mason et al. |
| 2004/0144391 A1 | 7/2004 | Brady et al. | | 2006/0085227 A1 | 4/2006 | Rosenfeld et al. |
| 2004/0147974 A1 | 7/2004 | Engmark et al. | | 2006/0095032 A1 | 5/2006 | Jackson et al. |
| 2004/0149282 A1 | 8/2004 | Hickle | | 2006/0100496 A1 | 5/2006 | Avron |
| 2004/0163648 A1 | 8/2004 | Burton | | 2006/0100530 A1 | 5/2006 | Kliot et al. |
| 2004/0173456 A1 | 9/2004 | Boos et al. | | 2006/0100618 A1 | 5/2006 | Chan et al. |
| 2004/0221370 A1 | 11/2004 | Hannula et al. | | 2006/0122517 A1 | 6/2006 | Banet et al. |
| 2004/0230116 A1 | 11/2004 | Cowan et al. | | 2006/0122520 A1 | 6/2006 | Banet et al. |
| 2004/0231772 A1 | 11/2004 | Leonard et al. | | 2006/0124128 A1 | 6/2006 | Deane et al. |
| 2004/0236207 A1 | 11/2004 | Widener et al. | | 2006/0125623 A1 | 6/2006 | Applet et al. |
| 2004/0236242 A1 | 11/2004 | Graham et al. | | 2006/0132382 A1 | 6/2006 | Jannard |
| 2004/0242981 A1 | 12/2004 | Pattisapu | | 2006/0133362 A1 | 6/2006 | Stein et al. |
| 2004/0254490 A1 | 12/2004 | Egli | | 2006/0142640 A1 | 6/2006 | Takahashi |
| 2004/0254501 A1 | 12/2004 | Mault | | 2006/0149132 A1 | 7/2006 | Iddan |
| 2004/0267145 A1 | 12/2004 | David et al. | | 2006/0149339 A1 | 7/2006 | Burnes et al. |
| 2005/0001728 A1 | 1/2005 | Applet et al. | | 2006/0167351 A1 | 7/2006 | Isaacson et al. |
| 2005/0020919 A1 | 1/2005 | Stringer et al. | | 2006/0173247 A1 | 8/2006 | Medina |
| 2005/0027207 A1 | 2/2005 | Westbrook et al. | | 2006/0183980 A1 | 8/2006 | Yang |
| 2005/0029432 A1 | 2/2005 | Bacarella et al. | | 2006/0184051 A1 | 8/2006 | Hempstead et al. |
| 2005/0041531 A1 | 2/2005 | Sekura et al. | | 2006/0189859 A1 | 8/2006 | Kiani et al. |
| 2005/0043599 A1 | 2/2005 | O'Mara | | 2006/0195026 A1 | 8/2006 | Casciani et al. |
| 2005/0043763 A1 | 2/2005 | Marcovecchio et al. | | 2006/0195027 A1 | 8/2006 | Casciani et al. |
| 2005/0049465 A1 | 3/2005 | Wang | | 2006/0211929 A1 | 9/2006 | Casciani et al. |
| 2005/0049501 A1 | 3/2005 | Conero et al. | | 2006/0211942 A1 | 9/2006 | Hoctor et al. |
| 2005/0059869 A1 | 3/2005 | Scharf et al. | | 2006/0217604 A1 | 9/2006 | Fein et al. |
| 2005/0070776 A1 | 3/2005 | Mannheimer et al. | | 2006/0217605 A1 | 9/2006 | Fein et al. |
| 2005/0070778 A1 | 3/2005 | Lakcey et al. | | 2006/0217606 A1 | 9/2006 | Fein et al. |
| 2005/0075550 A1 | 4/2005 | Lindekugel | | 2006/0217607 A1 | 9/2006 | Fein et al. |
| 2005/0080345 A1 | 4/2005 | Finburgh et al. | | 2006/0217608 A1 | 9/2006 | Fein et al. |
| 2005/0085799 A1 | 4/2005 | Luria et al. | | 2006/0224040 A1 | 10/2006 | Khait et al. |
| 2005/0090754 A1 | 4/2005 | Wolff et al. | | 2006/0224326 A1 | 10/2006 | St. Ores et al. |
| 2005/0096557 A1 | 5/2005 | Vosburgh et al. | | 2006/0224421 A1 | 10/2006 | St. Ores et al. |
| 2005/0101845 A1 | 5/2005 | Nihtila | | 2006/0229510 A1 | 10/2006 | Fein et al. |
| 2005/0102167 A1 | 5/2005 | Kapoor | | 2006/0229511 A1 | 10/2006 | Fein et al. |
| 2005/0113650 A1 | 5/2005 | Pacione et al. | | 2006/0241358 A1 | 10/2006 | Al-Ali et al. |
| 2005/0113703 A1 | 5/2005 | Farringdon et al. | | 2006/0241384 A1 | 10/2006 | Fisher et al. |
| 2005/0114154 A1 | 5/2005 | Wolkoweiz et al. | | 2006/0241510 A1 | 10/2006 | Halperin et al. |
| 2005/0171576 A1 | 8/2005 | Williams et al. | | 2006/0247504 A1 | 11/2006 | Tice |
| 2005/0182458 A1 | 8/2005 | Goedeke | | 2006/0253010 A1 | 11/2006 | Brady et al. |
| 2005/0188991 A1 | 9/2005 | Sun et al. | | 2006/0253953 A1 | 11/2006 | Williams |
| 2005/0190068 A1 | 9/2005 | Gentry et al. | | 2006/0258922 A1 | 11/2006 | Mason et al. |
| 2005/0197548 A1 | 9/2005 | Dietiker | | 2006/0264722 A1 | 11/2006 | Hannula et al. |
| 2005/0206518 A1 | 9/2005 | Welch et al. | | 2006/0264771 A1 | 11/2006 | Lin et al. |
| 2005/0215847 A1 | 9/2005 | Heruth et al. | | 2006/0276700 A1 | 12/2006 | O'Neil et al. |
| 2005/0215880 A1 | 9/2005 | Harrison et al. | | 2006/0276701 A1 | 12/2006 | Ray |
| 2005/0215947 A1 | 9/2005 | Heruth et al. | | 2007/0032732 A1 | 2/2007 | Shelley et al. |
| 2005/0216064 A1 | 9/2005 | Heruth et al. | | 2007/0060808 A1 | 3/2007 | Hoarau |
| 2005/0216199 A1 | 9/2005 | Banet | | 2007/0073117 A1 | 3/2007 | Raridan, Jr. |

| | | |
|---|---|---|
| 2007/0073121 A1 | 3/2007 | Hoarau et al. |
| 2007/0073123 A1 | 3/2007 | Raridan, Jr. |
| 2007/0073126 A1 | 3/2007 | Raridan, Jr. |
| 2007/0078316 A1 | 4/2007 | Hoarau |
| 2007/0100218 A1 | 5/2007 | Sweitzer et al. |
| 2007/0100219 A1 | 5/2007 | Sweitzer et al. |
| 2007/0149871 A1 | 6/2007 | Sarussi et al. |
| 2007/0219439 A1 | 9/2007 | Vilser et al. |
| 2007/0260129 A1 | 11/2007 | Chin et al. |
| 2007/0270665 A1 | 11/2007 | Yang et al. |
| 2007/0293746 A1 | 12/2007 | Sarussi et al. |
| 2008/0009691 A1 | 1/2008 | Parker |
| 2008/0076988 A1 | 3/2008 | Sarussi et al. |
| 2008/0076990 A1 | 3/2008 | Sarussi et al. |
| 2008/0081967 A1 | 4/2008 | Andersohn et al. |
| 2008/0139908 A1 | 6/2008 | Kurth |
| 2008/0143080 A1 | 6/2008 | Burr |
| 2008/0146890 A1 | 6/2008 | Leboeuf et al. |
| 2008/0165017 A1 | 7/2008 | Schwartz |
| 2008/0183058 A1 | 7/2008 | Mannheimer |
| 2008/0221413 A1 | 9/2008 | Hoarau |
| 2008/0221414 A1 | 9/2008 | Baker |
| 2008/0228053 A1 | 9/2008 | Wang et al. |
| 2008/0230363 A1 | 9/2008 | Yang et al. |
| 2010/0031904 A1 | 2/2010 | Matsuura et al. |
| 2010/0076337 A1 | 3/2010 | Medina |

FOREIGN PATENT DOCUMENTS

| | | |
|---|---|---|
| DE | 3516338 | 11/1986 |
| DE | 3703458 | 8/1988 |
| DE | 3705493 | 8/1988 |
| DE | 3744781 | 1/1989 |
| DE | 3810411 | 10/1989 |
| DE | 3927038 | 2/1991 |
| DE | 4429845 | 10/1995 |
| DE | 19632361 | 2/1997 |
| DE | 19541605 | 5/1997 |
| DE | 19939302 | 5/2001 |
| DE | 10029205 | 1/2002 |
| EP | 0127947 | 12/1984 |
| EP | 0204259 | 12/1986 |
| EP | 268850 | 6/1988 |
| EP | 0313238 | 4/1989 |
| EP | 338518 | 10/1989 |
| EP | 463620 | 1/1992 |
| EP | 0531631 | 3/1993 |
| EP | 543172 | 5/1993 |
| EP | 0572684 | 12/1993 |
| EP | 0573137 | 12/1993 |
| EP | 578530 | 1/1994 |
| EP | 580385 | 1/1994 |
| EP | 775311 | 8/1994 |
| EP | 621026 | 10/1994 |
| EP | 0631756 | 1/1995 |
| EP | 665025 | 8/1995 |
| EP | 0695139 | 2/1996 |
| EP | 0721110 | 7/1996 |
| EP | 1048323 | 2/2000 |
| EP | 996063 | 4/2000 |
| EP | 1130412 | 5/2001 |
| EP | 1169965 | 1/2002 |
| EP | 1683478 | 7/2006 |
| EP | 1945099 | 7/2008 |
| FR | 2555744 | 11/1983 |
| FR | 2601137 | 1/1988 |
| FR | 2685865 | 7/1993 |
| GB | 834469 | 5/1960 |
| GB | 2135074 | 8/1984 |
| GB | 2390903 | 1/2004 |
| JP | 55024614 | 2/1980 |
| JP | 04057161 | 2/1992 |
| JP | 6014906 | 1/1994 |
| JP | 07336597 | 12/1995 |
| JP | 08111295 | 4/1996 |
| JP | 08112257 | 5/1996 |
| JP | 08336546 | 12/1996 |
| JP | 09010319 | 1/1997 |
| JP | 09154937 | 6/1997 |
| JP | 10314149 | 12/1998 |
| JP | 11259583 | 9/1999 |
| JP | 2000189440 | 7/2000 |
| JP | 2001161648 | 6/2001 |
| JP | 2001190498 | 7/2001 |
| JP | 2001308576 | 11/2001 |
| JP | 2001332832 | 11/2001 |
| JP | 2001345756 | 12/2001 |
| JP | 2002065647 | 3/2002 |
| JP | 2003210402 | 7/2003 |
| JP | 2003235813 | 8/2003 |
| JP | 2003265425 | 9/2003 |
| JP | 2004016659 | 1/2004 |
| JP | 2004065832 | 3/2004 |
| JP | 2004121549 | 4/2004 |
| JP | 2004258761 | 9/2004 |
| JP | 2005013612 | 1/2005 |
| JP | 2005110816 | 4/2005 |
| JP | 2005111187 | 4/2005 |
| JP | 2005143782 | 6/2005 |
| JP | 2005168600 | 6/2005 |
| JP | 2005266860 | 9/2005 |
| JP | 2006061178 | 3/2006 |
| JP | 2006066512 | 3/2006 |
| JP | 2006122693 | 5/2006 |
| KR | 2003065871 | 5/2004 |
| KR | 2005106928 | 12/2004 |
| RU | 2132204 | 6/1999 |
| WO | WO9001293 | 2/1990 |
| WO | WO9111137 | 8/1991 |
| WO | WO9115151 | 10/1991 |
| WO | WO9118550 | 12/1991 |
| WO | WO9220273 | 11/1992 |
| WO | WO9502358 | 1/1995 |
| WO | WO9506430 | 3/1995 |
| WO | WO9512349 | 5/1995 |
| WO | WO9615714 | 5/1996 |
| WO | WO9616591 | 6/1996 |
| WO | WO9641138 | 12/1996 |
| WO | WO9720494 | 6/1997 |
| WO | WO9720497 | 6/1997 |
| WO | WO9736536 | 10/1997 |
| WO | WO9817174 | 4/1998 |
| WO | WO9947039 | 9/1999 |
| WO | WO0059374 | 10/2000 |
| WO | WO0078209 | 12/2000 |
| WO | WO0101855 | 1/2001 |
| WO | WO0117425 | 3/2001 |
| WO | WO0176471 | 10/2001 |
| WO | WO0187224 | 11/2001 |
| WO | WO0215784 | 2/2002 |
| WO | WO02065901 | 8/2002 |
| WO | WO02066977 | 8/2002 |
| WO | WO02089664 | 11/2002 |
| WO | WO03026558 | 4/2003 |
| WO | WO03057030 | 7/2003 |
| WO | WO03071928 | 9/2003 |
| WO | WO03080152 | 10/2003 |
| WO | WO2004030480 | 4/2004 |
| WO | WO2004046673 | 6/2004 |
| WO | WO2004084720 | 10/2004 |
| WO | WO2005046466 | 5/2005 |
| WO | WO2005079663 | 9/2005 |
| WO | WO2006007231 | 1/2006 |
| WO | WO2006017117 | 2/2006 |
| WO | WO2006021956 | 3/2006 |
| WO | WO2006094108 | 9/2006 |
| WO | WO2007048039 | 4/2007 |

OTHER PUBLICATIONS

Faisst, Karin, et al.; "Intrapartum Reflectance Pulse Oximetry: Effects of Sensor Location and Fixation Duration on Oxygen Saturation Readings," *Journal of Clinical Monitoring*, vol. 13, pp. 299-302 (1997).

Izumi, Akio, et al.; "Accuracy and Utility of a New Reflectance Pulse Oximeter for Fetal Monitoring During Labor," *Journal of Clinical Monitoring*, vol. 13, pp. 103-108 (1997).

"Smaller Product, Tighter Tolerances Pose Dispensing Challenges for Medical Device Manufacturer," *Adhesives Age*, pp. 40-41 (Oct. 1997).

Crilly, Paul B., et al.; "An Integrated Pulse Oximeter System for Telemedicine Applications," *IEEE Instrumentation and Measurement Technology Conference*, Ottawa, Canada; May 19-21, 1997; pp. 102-104.

DeKocK, Marc; "Pulse Oximetry Probe Adhesive Disks: a Potential for Infant Aspiration," *Anesthesiology*, vol. 89, pp. 1603-1604 (1998).

Rhee, Sokwoo, et al.; "The Ring Sensor: a New Ambulatory Wearable Sensor for Twenty-Four Hour Patient Monitoring," *Proceedings of the 20th annual International Conference of the IEEE Engineering in Medicine and Biology Society*, 1998, vol. 20, No. 4, pp. 1906-1919.

Yang, Boo-Ho, et al.; "A Twenty-Four Hour Tele-Nursing System Using a Ring Sensor," *Proceedings of the 1998 IEEE International Conference on Robotics & Automation, Leaven, Belgium*, May 1998; pp. 387-392.

Ferrell, T.L., et al.; "Medical Telesensors," *SPIE*, vol. 3253, pp. 193-198 (1998).

Rohling, Roman, et al.; "Clinical Investigation of a New Combined Pulse Oximetry and Carbon Dioxide Tension Sensor in Adult Anaesthesia," *Journal of Clinical Monitoring and Computing*, vol. 15; pp. 23-27 (1999).

Yang, Boo-Ho, et al.; "Development of the ring sensor for healthcare automation," *Robotics and Autonomous Systems*, vol. 30, pp. 273-281 (2000).

Rhee, Sokwoo, et al.; "Artifact-Resistant, Power-Efficient Design of Finger-Ring Plethysmographic Sensor-Part I: Design and Analysis," *Proceedings of the 22nd Annual EMBS International Conference*, Chicago, Illinois; Jul. 23-28, 2000; pp. 2792-2795.

Rhee, Sokwoo, et al.; "Artifact-Resistant, Power-Efficient Design of Finger-Ring Plethysmographic Sensor-Part II: Prototyping and Benchmarking," *Proceedings of the 22nd Annual EMBS International Conference*, Chicago, Illinois; Jul. 23-28, 2000; pp. 2796.

Schulz, Christian Eric; "Design of a Pulse Oximetry Sensor Housing Assembly," California State University Master's Thesis, *UMI Dissertation Services*, UMI No. 1401306, (May 2000) 63 pages.

Yokota, Nakaura, Takahashi, et al.; "Pilot Model of a Reflectance-Type Pulse Oximeter for Pre-hospital Evaluation," *Journal of the Japanese Society of Emergency Medicine*, Kanto Region, vol. 21, pp. 26-27 (2000) (Article in Japanese—contains English summary.

Gisiger, P.A., et al.; "OxiCarbo®, a single sensor for the non-invasive measurement of arterial oxygen saturation and $CO_2$ partial pressure at the ear lobe," *Sensor and Actuators*, vol. B-76, pp. 527-530 (2001).

Rhee, Sokwoo, et al.; "Artifact-Resistant, Power-Efficient Design of Finger-Ring Plethysmographic Sensor," *IEEE Transactions on Biomedical Engineering*, vol. 48, No. 7, pp. 795-805 (Jul. 2001).

Gosney, S., et al.; "An alternative position for the pulse oximeter probe," *Anaesthesia*, vol. 56, p. 493 (2001).

Maletras, Francois-Xavier, et al.; "Construction and calibration of a new design of Fiber Optic Respiratory Plethysmograph (FORP)," *Optomechanical Design and Engineering, Proceedings of SPIE*, vol. 4444, pp. 285-293 (2001).

Earthrowl-Gould, T., et al.; "Chest and abdominal surface motion measurement for continuous monitoring of respiratory function," *Proc. Instn Mech Engrs*, V215, Part H; pp. 515-520 (2001).

Kyriacou, Panayiotis A., et al.; "Esophageal Pulse Oximetry Utilizing Reflectance Photoplethysmography," *IEEE Transactions on Biomedical Engineering*, vol. 49, No. 11, pp. 1360-1368 (Nov. 2002).

Kyriacou, P. A., et al.; "Investigation of esophageal photoplethysmographic signals and blood oxygen saturation measurements in cardiothoracic surgery patients," *Physiological Measurement*, vol. 23, No. 3, pp. 533-545 (Aug. 2002).

Irie, A., et al.; "Respiration Monitors—Pulse Oximeters," *Neonatal Care*, vol. 15, No. 12, pp. 78-83 (2002) (Article in Japanese—contains English summary of article).

Shaltis, Phillip, et al.; "Implementation and Validation of a Power-Efficient, High-Speed Modulation Design for Wireless Oxygen Saturation Measurement Systems," *IEEE*, pp. 193-194 (2002).

Warren, Steve, et al.; "Wearable Sensors and Component-Based Design for Home Health Care," *Proceedings of the Second Joint EMBS/BMES Conference*, Houston, Texas; Oct. 23-26, 2002; pp. 1871-1872.

Bentley, David J. et al.; "Measure Pressure with Thin Film"; Paper Film & Foil Converter; May 1, 2003.

Matsui, A., et al.; "Pulse Oximeter," *Neonatal Care*, vol. 16, No. 3, pp. 38-45 (2003) (Article in Japanese—contains English summary of article).

Nakagawa, M., et al.; "Oxygen Saturation Monitor," *Neonatal Monitoring*, vol. 26, No. 5, pp. 536-539 (2003) (Article in Japanese—contains English summary of article).

Mannheimer, Paul D., et al.; "The influence of Larger Subcutaneous Blood Vessels on Pulse Oximetry," *Journal of clinical Monitoring and Computing*, vol. 18, pp. 179-188 (2004).

Wendelken, Suzanne, et al.; "The Feasibility of Using a Forehead Reflectance Pulse Oximeter for Automated Remote Triage," *IEEE*, pp. 180-181 (2004).

Sugino, Shigekzau, et al.; "Forehead is as sensitive as finger pulse oximetry during general anesthesia," *Can J. Anesth.; General Anesthesia*, vol. 51, No. 5; pp. 432-436 (2004).

Kocher, Serge, et al.; "Performance of a Digital $PCO_2/SPO_2$ Ear Sensor," *Journal of Clinical Monitoring and Computing*, vol. 18, pp. 75-59 (2004).

Johnston, William S., et al.; "Effects of Motion Artifacts on helmet-Mounted Pulse Oximeter Sensors," 2 pgs. (2004).

Branche, Paul C., et al.; "Measurement Reproducibility and Sensor Placement Considerations in Designing a Wearable Pulse Oximeter for Military Applications," 2 pgs. (2004).

Heuss, Ludwig T., et al.; "Combined Pulse Oximetry / Cutaneous Carbon dioxide Tension Monitoring During Colonoscopies: Pilot study with a Smart Ear Clip," *Digestion*, vol. 70, pp. 152-158 (2004).

Urquhart, C., et al.; "Ear probe pulse oximeters and neonates," *Anaesthesia*, vol. 60, p. 294 (2005).

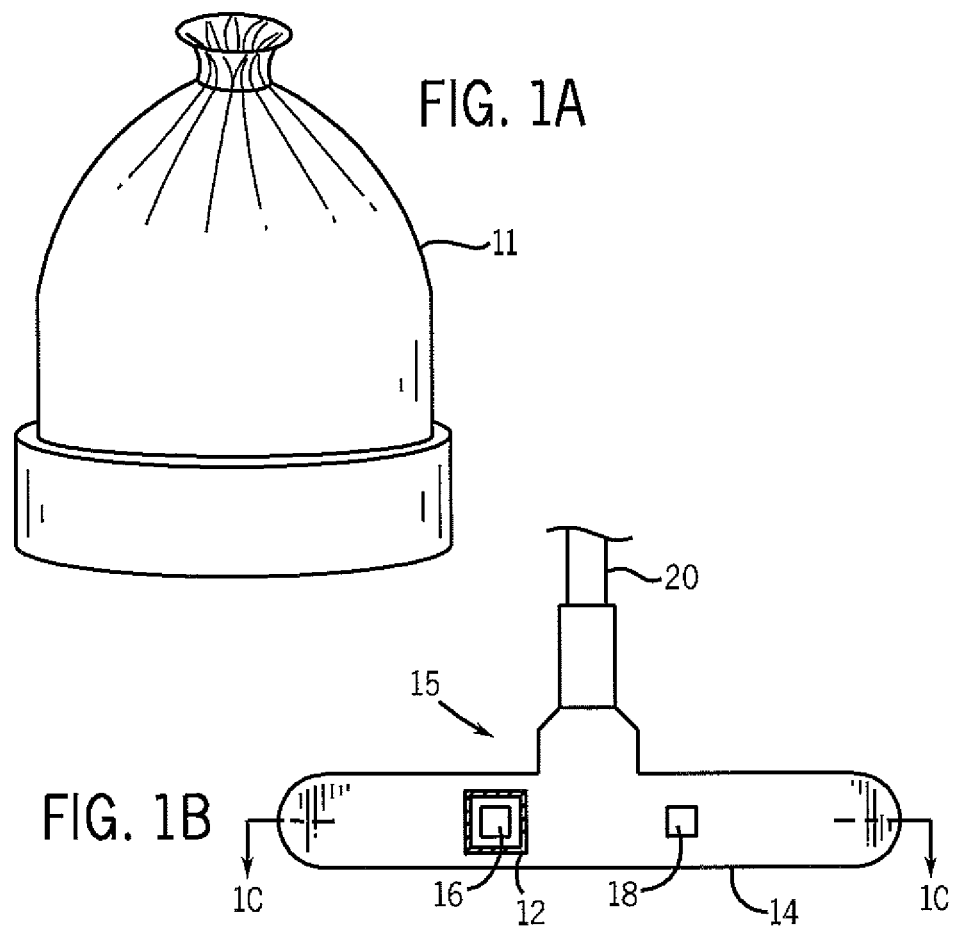
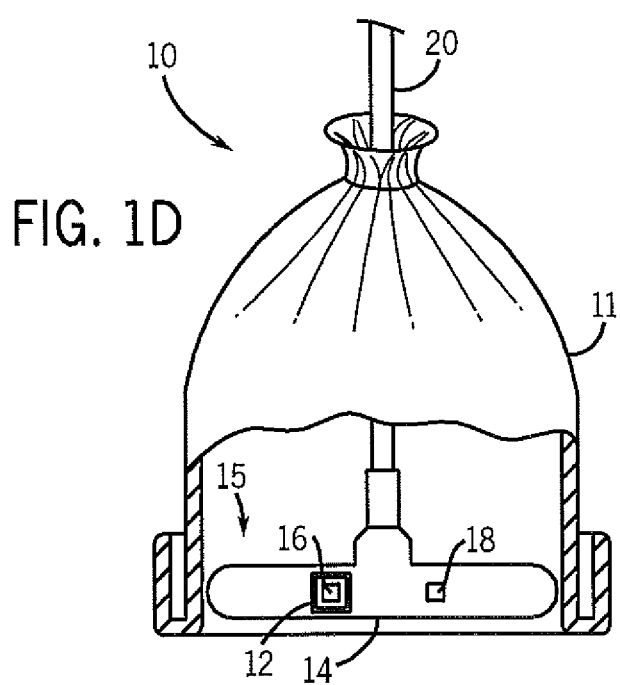

MEDICAL SENSOR WITH COMPRESSIBLE LIGHT BARRIER AND TECHNIQUE FOR USING THE SAME

CROSS-REFERENCE TO RELATED APPLICATIONS

This claims the benefit of U.S. Provisional patent Application No. 61/163,358, filed Mar. 25, 2009, which is hereby incorporated by reference herein in its entirety.

BACKGROUND

The present disclosure relates generally to medical devices and, more particularly, to sensors used for sensing physiological parameters of a patient.

This section is intended to introduce the reader to aspects of the art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

In the field of medicine, doctors often desire to monitor certain physiological characteristics of their patients. Accordingly, a wide variety of devices have been developed for monitoring many such physiological characteristics. Such devices provide doctors and other healthcare personnel with the information they need to provide the best possible healthcare for their patients. As a result, such monitoring devices have become an indispensable part of modern medicine.

One technique for monitoring certain physiological characteristics of a patient is commonly referred to as pulse oximetry, and the devices built based upon pulse oximetry techniques are commonly referred to as pulse oximeters. Pulse oximetry may be used to measure various blood flow characteristics, such as the blood-oxygen saturation of hemoglobin in arterial blood, the volume of individual blood pulsations supplying the tissue, and/or the rate of blood pulsations corresponding to each heartbeat of a patient. In fact, the "pulse" in pulse oximetry refers to the time varying amount of arterial blood in the tissue during each cardiac cycle.

Pulse oximeters typically utilize a non-invasive sensor that transmits light through a patient's tissue and that photoelectrically detects the absorption and/or scattering of the transmitted light in such tissue. One or more of the above physiological characteristics may then be calculated based upon the amount of light absorbed and/or scattered. More specifically, the light passed through the tissue is typically selected to be of one or more wavelengths that may be absorbed and/or scattered by the blood in an amount correlative to the amount of the blood constituent present in the blood. The amount of light absorbed and/or scattered may then be used to estimate the amount of blood constituent in the tissue using various algorithms.

Pulse oximetry readings involve placement of a sensor on a patient's tissue, typically via a lightly adhesive sensor, a clip-style sensor, or a sensor that may be fitted into a wearable garment, such as a hat or a headband. If the hat or headband is not closely fitted to the patient's tissue, ambient light may interfere with the sensor's light detection. Some outside light infiltration into the sensor may be avoided by fitting the sensor snugly against the patient's tissue. However, such a conforming fit may be difficult to achieve over a range of patient physiologies without adjustment or excessive attention on the part of medical personnel. Additionally, an overly tight fit may cause local exsanguination of the tissue around the sensor. Exsanguinated tissue, which is devoid of blood, may shunt the sensor light through the tissue, which may also result in increased measurement errors.

BRIEF DESCRIPTION OF THE DRAWINGS

Advantages of the disclosure may become apparent upon reading the following detailed description and upon reference to the drawings in which:

FIG. 1A illustrates a perspective view of a hat structure for holding a pulse oximetry sensor on a patient's tissue according to an embodiment;

FIG. 1B illustrates a perspective view of an exemplary pulse oximetry sensor body with an compressible light barrier that may be incorporated with the hat of FIG. 1A;

FIG. 1D illustrates a cutaway view of the hat of FIG. 1A with the pulse oximetry sensor with a compressible light barrier as shown in FIG. 1B and FIG. 1C;

DETAILED DESCRIPTION OF SPECIFIC EMBODIMENTS

Figure 1C:
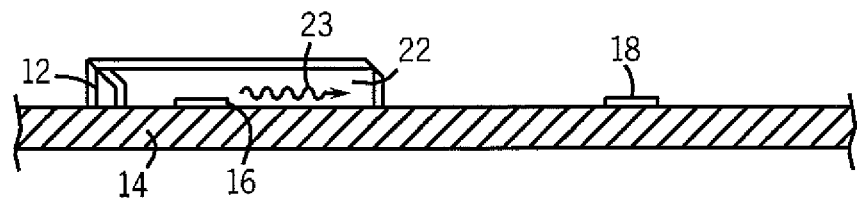
FIG. 1C illustrates a cross-sectional view of the pulse oximetry sensor body taken along line 1C-1C of FIG. 1B.

One or more specific embodiments of the present disclosure will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

Optical medical sensors are provided that reduce the amount of outside light that may impinge the detecting elements of a sensor. Such sensors may also reduce the amount of "shunted" light, i.e., light originating from light emitting elements of the sensor that impinges the detecting elements of a sensor without first passing through tissue. Such sensors may incorporate surface features on the tissue-contacting surface of the sensor to influence the path of light from the undesired light sources and/or to direct such light away from the detecting elements of the sensor. Such sensors may absorb or reflect the light originating from these undesired light sources before such light can impinge the detecting elements of the sensor.

Pulse oximetry sensors are typically placed on a patient in a location that is normally perfused with arterial blood to facilitate measurement of the desired blood characteristics, such as arterial oxygen saturation measurement ($SpO_2$). The most common sensor sites include a patient's fingertips, toes, earlobes, or forehead. Regardless of the placement of a sensor used for pulse oximetry, the reliability of the pulse oximetry measurement is related to the accurate detection of transmitted light that has passed through the perfused tissue and that has not been supplemented by undesired light sources. Such supplementation and/or modulation of the signals transmitted to a monitor by the sensor can cause variability in the resulting pulse oximetry measurements. The contribution of ambient and/or shunted light may affect the measurement of the particular blood constituent, such as $SpO_2$.

In many cases, light from undesired light sources propagates along an optical path that is distinguishable from the optical path of the light that is related to a blood constituent. In a transmission-type sensor, the sensor's emitter and detector lie on opposing sides of the tissue when the sensor is applied to a patient. The optical path of the signal light, which is light originating from the emitter that properly passes through perfused tissue, is substantially in-line with an imaginary axis connecting the emitter and the detector. For reflectance-type sensors, the optical path of the emitted signal light is somewhat more complicated, as the light first enters the perfused tissue and then is scattered back to the detector. In both transmission-type and reflectance-type sensors, shunted light and ambient light generally propagate at angles substantially off-axis from the optical path of the signal light.

The sensors discussed below have compressible light barriers that act to divert shunted and/or ambient light away from the light detecting elements of a sensor. In an embodiment, an oximetry sensor with such compressible light barriers may be adapted for placement in a hat (for example, a neonatal stocking cap), a headband, or other wearable structure (i.e. a glove, a sock, a wristband) to apply the sensor on the body of the user. FIGS. 1A-1D illustrate an assembly drawing of an embodiment of a sensor assembly 10 including a wearable structure, which may be a hat 11, as shown in FIG. 1A. A reflectance-type pulse oximetry sensor 15, as shown in FIG. 1B, is adapted to be placed or adhered to the inside of the hat 11. The sensor 15 may include a substrate 14 that may be made from any suitable material. In an embodiment, the substrate 14 is a foam or other conformable material. In one embodiment, the substrate 14 is black or dark in color to absorb stray light and further minimize any shunting of light between sensor and patient skin. The substrate 14 may include an adhesive material to secure the sensor directly to the tissue. In one embodiment, the sensor 15 may include an emitter 16 containing emitters for two or more wavelengths of lights and a detector 18 spaced apart from the emitter 16. The sensor 15 also may include compressible light barrier 12, discussed in more detail below, configured to block undesired light from reaching the detector 18.

Also shown in FIG. 1B is a cable 20 for providing drive current to the LED component of the emitter 16, and providing the detector signal to the medical device. In addition to providing the electrical connection to the downstream medical device, the cable 20 may provide shielding to protect the signals from the detector against external electrical interference. In addition, the sensor 15 may include suitable structures for providing electrical connections to the cable 20 and/or downstream medical device, such as a flex circuit, a Faraday shield, and leads connecting the optical components of the sensor 15 to the electrical components.

FIG. 1C is a cross-sectional side view showing the compressible light barrier 12 that substantially surrounds emitter 16. The compressible light barrier 12 may protrude from the surface 14 of the sensor 15. When the hat 11 is applied to the tissue, the force of the elastic band or knit of the hat 11 may provide sufficient force such that the compressible light barrier 12 is compressed against the tissue to form a seal. Any light from the emitter 16 on a path, represented by arrow 23, to shunt directly to the detector 18 is blocked by the interior walls 22 of the compressible light barrier 12. Accordingly, light from the emitter 16 may be directed towards the tissue and away from the shunt path to the detector 18, which may improve the accuracy of measurements from the sensor 15.

As shown, the compressible light barrier 12 surrounds the emitter 16. However, in embodiments the compressible light barrier 12 may surround the detector 18, or both the emitter 16 and the detector 18, or may be disposed in a region between the emitter 16 and the detector 18. In an embodiment, it may be advantageous for the footprint of the compressible light barrier 12 on the surface 14 to be minimized. For example, while the compressible light barrier 12 may act to prevent unwanted light from reaching the detector, the compressible light barrier 12, because it protrudes from the surface 14, may also interfere with a conforming fit of the sensor 15 to the tissue. Accordingly, a balance between the light barrier properties and the conforming fit may be achieved by providing the compressible light barrier 12 on less than 25%, less than 20%, less than 15%, less than 10%, or less than 5% of the surface 14. This may be achieved by providing the compressible light barrier 12 with relatively thin walls, or by surrounding only one of the emitter 16 and the detector 18 rather than both. In an embodiment, the compressible light barrier 12 surrounding the emitter 16 may have a different, or smaller, shape than the compressible light barrier 12 surrounding the detector 18. For example, it may be advantageous to have a smaller compressible light barrier 12 surrounding the emitter 16 to more narrowly focus the light directed towards the tissue. In addition, the compressible light barrier 12 may be configured to protrude minimally from the surface 14. The compressible light barrier 12 may protrude from the surface 14 at least about 0.5 mm, 1 mm, 2 mm, or 5 mm in its uncompressed state. It should be understood that the compressible light barrier 12, when compressed by the force of application of the sensor 15 to the tissue, may protrude only slightly from the surface 14. For example, the compressible light barrier 12 may protrude from the surface 14 about 0.5 mm, 1 mm, 2 mm, in its uncompressed state. A compressible light barrier 12 that is 5 mm in height in its uncompressed state may be compressed to a height of 2.5 mm (50% of its uncompressed height) or 1.25 mm (25% of its uncompressed height). Similarly, a compressible light barrier 12 that is 2 mm in height in its uncompressed state may be compressed to a height of 1 mm (50% of its uncompressed height) or 0.5 mm (25% of its uncompressed height).

In an embodiment, the compressible light barrier 12 is formed from materials with low durometer or a high degree of compressibility, such as foams, silicone, polyvinyl chloride, or gels, for example, a material having a compression modulus of about 2.0 or less. The compression modulus for polyurethane foam is a function of the density of the foam and the structure of the foam. Generally, compression modulus increases as foam density increases. In embodiments, different chemical formulations and manufacturing processes may be used to create foams with different foam cell structures. Foams with high concentration of closed cells (closed-cell foam) typically have a higher compression modulus than foams with high concentration of open cells (open-cell foam). In an embodiment, compressibility may be measured by an Indention Load Deflection (ILD) test, which measures the load-bearing capacity of a standard specimen indented by a circular compressor foot of 50 square inches as 25% deflection. The sample is placed on a perforated plate (perforated plate has ¼" holes on ¾" centers) and is deflected twice to 25% of its original height and then allowed to relax for 10+/− minutes. The height of the foam is then rechecked. The new height is determined and then the sample is deflected 25%, or to 75% of the crushed height. The foam is then held in this fashion for one minute and the load on the scale is then read. In one embodiment, the ratio (compression modules) of the compressive force needed to indent the foam to 25% and 50%, respectively, of its thickness is determined. The greater the value of this ratio, the greater the degree of firmness that is offered by the foam. Low density foams have a compression modulus of around 1.20. In embodiments, the compression modulus of the compressible light barrier 12 may be less than about 2.0, less than about 1.5 or less than about 1.2.

The sensor assembly 10 is shown fully assembled in FIG. 1D. As shown, the sensor 15 is positioned on the interior of the hat 11 such that the emitter 16 and detector 18 may come into contact with the skin when the sensor assembly 10 is applied to a patient. The sensor 15 may be attached (e.g., adhered or sewn into) to the inside band of the hat 11. In one embodiment, the hat 11 may include indicators to position the sensor 15 on a particular location on the patient's forehead, for example to position the sensor 15 on the lower forehead region, above the eyebrow, with the sensor optics (emitter 16 and detector 18) located above and predominantly lateral to or centered over the iris. The location of the reflectance sensor 15 in the hat allows appropriate placement of the sensor in the desired forehead location by a user. FIG. 1D shows that the cable 20 is positioned through a hole in the top of the hat 11. In an embodiment, the cable 20 may be adhered or otherwise constrained in the hat 11 so that the cable 20 generally is positioned away from the sensor 15 to avoid interfering with the patient's eyesight or bothering the patient.

In an embodiment, the force of the sensor 15 against the tissue, including any force provided by the compressible light barrier 12, may not exsanguinate the tissue. In one embodiment, it is contemplated that the force that hat 11 (or other wearable assembly, such as a headband or clip-style sensor) exerts on the tissue sufficient pressure so that the pressure exceeds the typical venous pressure of a patient, but does not exceed the diastolic arterial pressure. As the pulse oximetry measurements are related to arterial blood oxygen saturation and pulsation, and not venous blood pulsation, reducing the effect of the venous component in the tissue may enhance the sensitivity of the sensor to variations in the arterial blood signal. Thus, the sensor assembly 10 may apply a pressure greater than the venous pressure to squeeze excess pooled venous blood from the optically probed tissue. Yet, since the pressure applied by the sensor assembly 10 is designed to be less than the arterial pressure, the application of pressure to the tissue does not interfere with the arterial pulse signal. Typical venous pressure, diastolic arterial pressure, and systolic arterial pressure are less than 10-35 mmHg, 80 mmHg, and 120 mmHg, respectively. Accordingly, in certain embodiments, the sensor assembly 10 may be adjusted to overcome an average venous pressure of 15-35 mmHg. However, venous pressures may vary because of the location of the vascular bed and the patient's condition. For example, low arterial diastolic blood pressure (about 30 mmHg) may occur in sick patients. In such embodiments, the sensor assembly 10 removes most of the venous pooling with by applying sufficient pressure to overcome light to moderate venous pressure (about 15 mmHg).

In one embodiment, the force applied to the tissue to overcome the venous pressure may be sufficient to compress the compressible light barrier 12 to an appropriate degree, for example to at least 50% of its original uncompressed height or at least 25% of its original uncompressed height, so that the light barrier properties remain intact. In another embodiment, if the force applied to the sensor is increased, the compressible light barrier 12 may act as a pressure absorber, preventing the skin from becoming exsanguinated in the case of an inappropriately high pressure. In such an embodiment, the compressible light barrier 12 may then be compressed to an even greater degree, so that it lies substantially flush with the surface 14.

Figure 2:
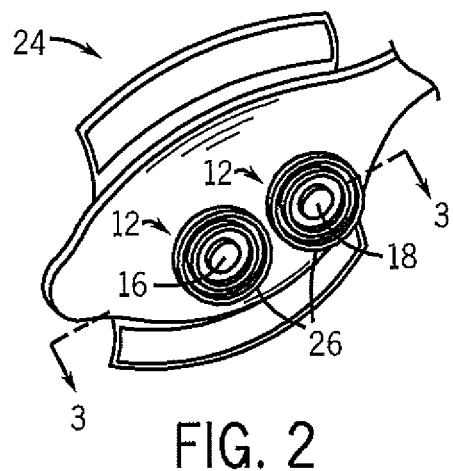
FIG. 2 illustrates a perspective view of a forehead sensor with a compressible light barrier arranged in concentric circles according to an embodiment.
Figure 3:
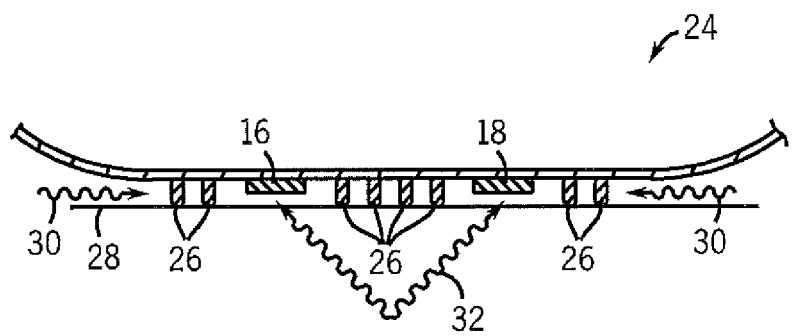
FIG. 3 illustrates a cross-sectional view of the sensor of FIG. 2 taken along line 3-3.

It should be appreciated that the compressible light barrier 12 may be arranged in any suitable manner on the surface of the sensor 15 to prevent ambient or shunted light from reaching the detector 18. In an embodiment, shown in FIG. 2 and FIG. 3, compressible light barrier 12 may be arranged to surround the emitter 16 and the detector 18. FIG. 2 is a perspective view of an exemplary forehead sensor 24 with a compressible light barrier 12 that includes concentric circles 26 that substantially surround an emitter 16 and a detector 18, and FIG. 3 is a cross-sectional view of the sensor 24 applied to a patient's forehead 28. Such an arrangement of concentric circles 26 may be advantageous in forming a seal with the tissue 28, thus creating a barrier against any ambient light or shunted light that may leak into the sensor 24. The ambient light, depicted by wavy arrows 30, impinges the compressible light barrier 12 and is prevented from reaching the detector 18. The optical path of the signal light, depicted by wavy arrow 32, is substantially unaffected by the compressible light barrier 12.

Figure 4:
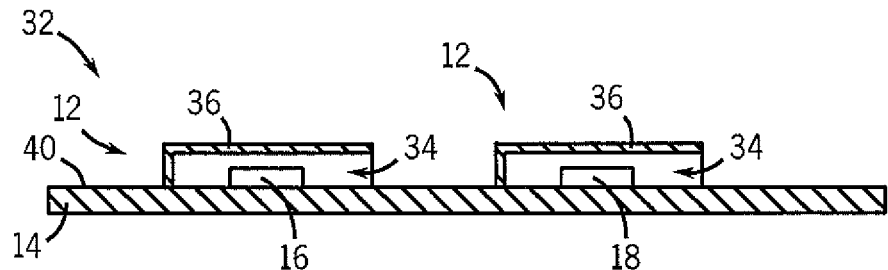
FIG. 4 illustrates a cross-sectional of a sensor with a compressible light barrier with light reflective and light absorptive surfaces according to an embodiment.

In one embodiment, the compressible light barrier 12 may include light absorbing materials, light reflecting materials, light refracting materials, or any combination thereof. For example, a surface, including all or part of a compressible light barrier 12, may be formed from, coated with, or impregnated with such materials. It should also be appreciated that, as discussed above, the compressible light barrier 12 may contain such materials only on a tissue-contacting surface, or, in alternate embodiments, the sensor body may be constructed entirely from such materials in appropriate regions as described herein. As shown in FIG. 4, a cross-sectional view of a sensor 32, the compressible light barrier 12 surrounding the emitter 16 may include a light reflective surface 34 and a light absorptive surface 36. As shown, the light surface 34 may face the emitter 16, while the light absorptive surface 36 may be surfaces that do not face the emitter 16. Such an arrangement may allow off-angle light from the emitter 16 to be reflected back towards the tissue, which may help to increase the signal intensity received at the detector 18. In addition, dark or absorptive surfaces on other areas of the compressible light barrier 12 may absorb ambient light that leaks from the edges of the sensor 32. Similarly, the compressible light barrier 12 surrounding the detector 18 may include a light reflective surface 34 to help redirect light towards the detector 18 while absorptive surface 36 may absorb shunted or ambient light before it reaches the detector 18. Examples of light absorbing materials may include, but are not limited to, black or dark pigment, black or dark woven fabric or cloth, and infrared blockers. Examples of suitable light reflecting materials include white or silver pigment, metals, or mirrored surfaces. Further, the surface 40 of the sensor 32 may be light reflective or light absorptive.

It should also be appreciated that light absorbing materials may be adapted to absorb light at a particular wavelength. In certain embodiments, when light absorbing material is disposed between an emitter and a detector of a sensor, it may be advantageous to use light absorbing material that absorbs a wavelength emitted by the emitter in order to absorb shunted light from the emitter. For example, a light absorbing material may absorb at least about 50% of one or more wavelengths of light from the emitter, or may absorb a range of 50% to 95% of one or more wavelengths of light from the emitter. A light absorbing material may also absorb at least about 90% to at least 95% of one or more wavelengths of visible light and near-infrared light. In a specific embodiment, a pulse oximetry sensor may emit at least one wavelength of light in the wavelength range of 500 nm-1000 nm. For example, a sensor may emit light and wavelengths of 660 nm and 900 nm, which are wavelengths that may be absorbed by dark pigment.

Figure 5:
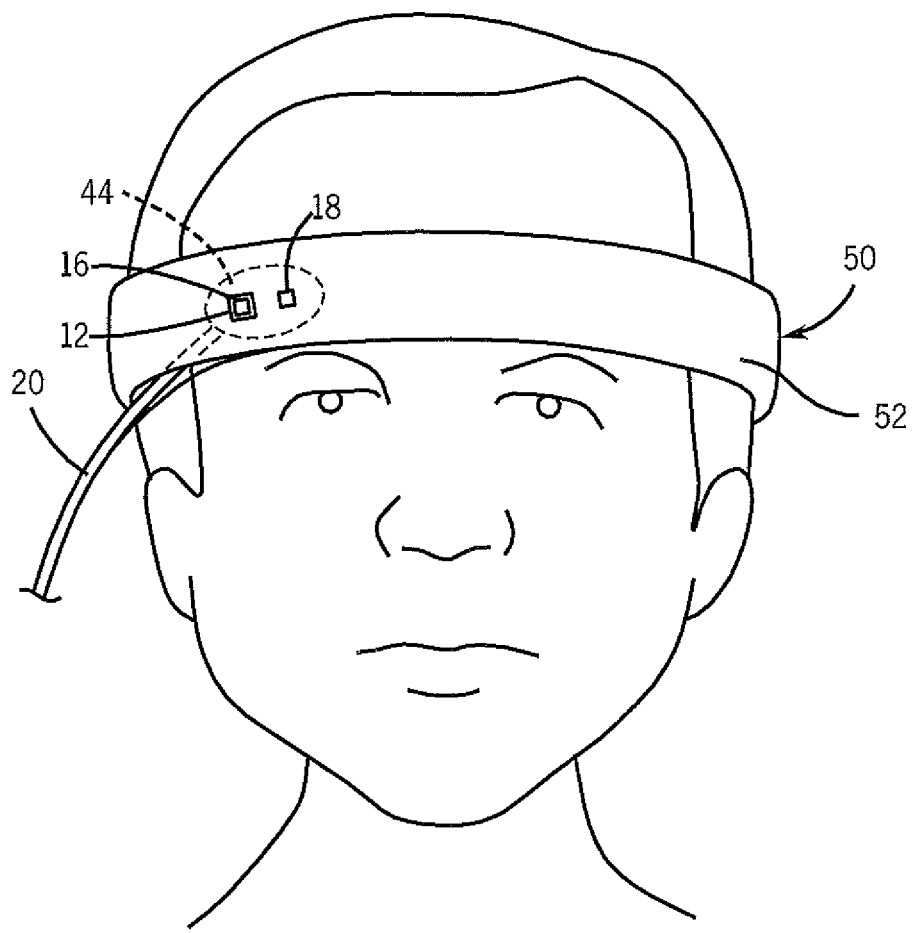
FIG. 5 illustrates a perspective view of a headband-style sensor with a compressible light barrier according to an embodiment.

FIG. 5 illustrates an embodiment of a headband-based sensor assembly 50 that includes a medical sensor 44 and with a compressible light barrier 12. The headband-based sensor assembly 50 may include a strap or band 52 that may be fitted around a patient's forehead tissue to contact the sensor 34 with the tissue. In certain embodiments, the sensor 44 may send feedback to a downstream monitor through cable 20 relating to one or more blood or tissue constituents.

Figure 6:
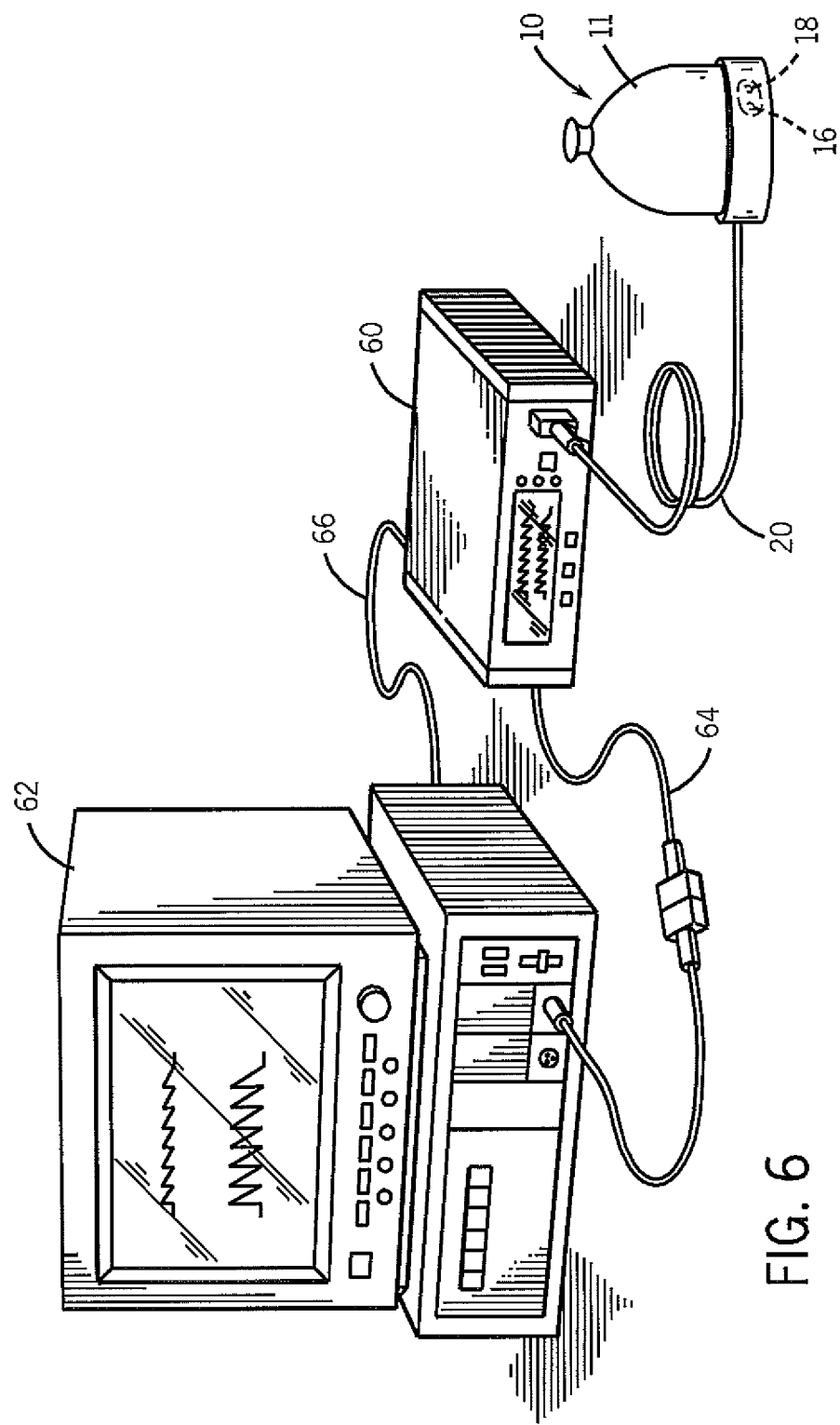
FIG. 6 illustrates a pulse oximetry system coupled to a multi-parameter patient monitor and a sensor according to an embodiment.

A sensor or sensor assembly, illustrated generically as a sensor assembly 10, may be used in conjunction with a pulse oximetry monitor 60, as illustrated in FIG. 6. It should be appreciated that the cable 20 of the sensor assembly 10 may be coupled to the monitor 60 or it may be coupled to a transmission device to facilitate wireless transmission between the sensor assembly 10 and the monitor 60. The monitor 60 may be any suitable pulse oximeter, such as those available from Nellcor Puritan Bennett LLC. Furthermore, to upgrade conventional pulse oximetry provided by the monitor 60 to provide additional functions, the monitor 60 may be coupled to a multi-parameter patient monitor 62 via a cable 64 connected to a sensor input port or via a cable 66 connected to a digital communication port.

Figure 7:
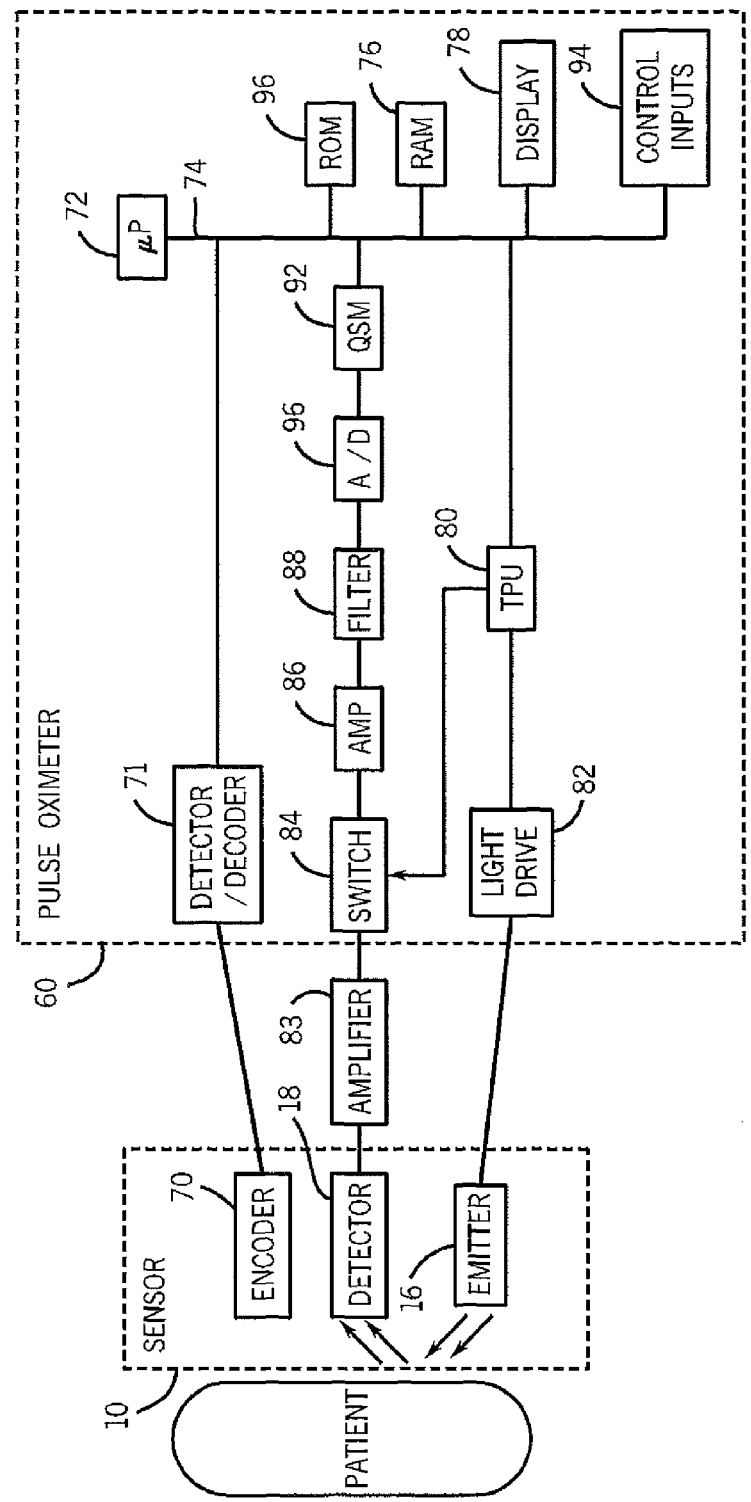
FIG. 7 is a block diagram of a pulse oximetry system according to an embodiment.

FIG. 7 is a block diagram of an embodiment of a pulse oximeter 60 that may be configured to implement the embodiments of the present disclosure. Light from emitter 16 may pass into a blood perfused tissue, and may be scattered, and then detected by detector 18. A sensor assembly 10 containing an emitter 16 and a detector 18 may also contain an encoder 70 which may be capable of providing signals indicative of the wavelength(s) of light source 16 to allow the oximeter to select appropriate calibration coefficients for calculating oxygen saturation. The encoder 70 may, in an embodiment, be a resistor.

In an embodiment, the sensor assembly 10 may be connected to a pulse oximetry monitor 60. The monitor 60 may include a microprocessor 72 coupled to an internal bus 74. Also connected to the bus may be a RAM memory 76 and a display 78. A time processing unit (TPU) 80 may provide timing control signals to light drive circuitry 82, which controls when the emitter 16 is activated, and if multiple light sources are used, the multiplexed timing for the different light sources. TPU 80 may also control the gating-in of signals from detector 18 through an amplifier 83 and a switching circuit 84. These signals are sampled at the proper time, depending at least in part upon which of multiple light sources is activated, if multiple light sources are used. The received signal from the detector 18 may be passed through an amplifier 86, a low pass filter 88, and an analog-to-digital converter 90. The digital data may then be stored in a queued serial module (QSM) 92, for later downloading to RAM 76 or ROM 96 as QSM 92 fills up.

In an embodiment, based at least in part upon the received signals corresponding to the light received by detector 18, microprocessor 72 may calculate the oxygen saturation using various algorithms. These algorithms may require coefficients, which may be empirically determined, and may correspond to the wavelengths of light used. The algorithms may be stored in a ROM 96 and accessed and operated according to microprocessor 72 instructions. For example, the encoder 70 may communicate with decoder 71 to allow the microprocessor 72 to determine the appropriate coefficients.

In an embodiment of a two-wavelength system, the particular set of coefficients chosen for any pair of wavelength spectra may be determined by a value indicated by the encoder 70 corresponding to a particular light source in a particular sensor assembly 10. In one embodiment, multiple resistor values may be assigned to select different sets of coefficients, or the sets of coefficients may be stored on a digital medium. In another embodiment, the resistors are used to select from among the coefficients appropriate for an infrared source paired with either a near red source or far red source. The selection between whether the near red or far red set will be chosen can be selected with a control input from control inputs 94. Control inputs 94 may be, for instance, a switch on the pulse oximeter, a keyboard, or a port providing instructions from a remote host computer. Furthermore, any number of methods or algorithms may be used to determine a patient's pulse rate, oxygen saturation or any other desired physiological parameter.

The sensor assembly 10 includes an emitter 16 and a detector 18 that may be of any suitable type. For example, the emitter 16 may be one or more light emitting diodes adapted to transmit one or more wavelengths of light in the red to infrared range, and the detector 18 may one or more photodetectors selected to receive light in the range or ranges emitted from the emitter 16. Alternatively, an emitter 16 may also be a laser diode or a vertical cavity surface emitting laser (VCSEL). An emitter 16 and detector 18 may also include optical fiber sensing elements. An emitter 16 may include a broadband or "white light" source, in which case the detector could include any of a variety of elements for selecting specific wavelengths, such as reflective or refractive elements or interferometers. These kinds of emitters and/or detectors would typically be coupled to the rigid or rigidified sensor via fiber optics. Alternatively, a sensor assembly 10 may sense light detected from the tissue is at a different wavelength from the light emitted into the tissue. Such sensors may be adapted to sense fluorescence, phosphorescence, Raman scattering, Rayleigh scattering and multi-photon events or photoacoustic effects.

For pulse oximetry applications using either transmission or reflectance type sensors the oxygen saturation of the patient's arterial blood may be determined using two or more wavelengths of light, most commonly red and near infrared wavelengths. Similarly, in other applications, a tissue water fraction (or other body fluid related metric) or a concentration of one or more biochemical components in an aqueous environment may be measured using two or more wavelengths of light, most commonly near infrared wavelengths between about 1,000 nm to about 2,500 nm. It should be understood that, as used herein, the term "light" may refer to one or more of ultrasound, radio, microwave, millimeter wave, infrared, visible, ultraviolet, gamma ray or X-ray electromagnetic radiation, and may also include any wavelength within the radio, microwave, infrared, visible, ultraviolet, or X-ray spectra.

The emitter 16 and the detector 18, and the compressible light barrier 12, may be disposed on a sensor body, which may be made of any suitable material, such as plastic, foam, woven material, or paper. Alternatively, the emitter 16 and the detector 18 may be remotely located and optically coupled to the sensor assembly 10 using optical fibers. In the depicted embodiments, the sensor assembly 10 is coupled to a cable that is responsible for transmitting electrical and/or optical signals to and from the emitter 16 and detector 18 of the sensor assembly 10. The cable may be permanently coupled to the sensor assembly 10, or it may be removably coupled to the sensor assembly 10—the latter alternative being more useful and cost efficient in situations where the sensor assembly 10 is disposable.

The sensor assembly 10 may be a "transmission type" sensor. Transmission type sensors include an emitter 16 and detector 18 that are typically placed on opposing sides of the sensor site. If the sensor site is a fingertip, for example, the sensor assembly 10 is positioned over the patient's fingertip such that the emitter 16 and detector 18 lie on either side of the patient's nail bed. In other words, the sensor assembly 10 is positioned so that the emitter 16 is located on the patient's fingernail and the detector 18 is located 180° opposite the emitter 16 on the patient's finger pad. During operation, the emitter 16 shines one or more wavelengths of light through the patient's fingertip and the light received by the detector 18 is processed to determine various physiological characteristics of the patient. In each of the embodiments discussed herein, it should be understood that the locations of the emitter 16 and the detector 18 may be exchanged. For example, the detector 18 may be located at the top of the finger and the emitter 16 may be located underneath the finger. In either arrangement, the sensor assembly 10 will perform in substantially the same manner.

Reflectance type sensors also operate by emitting light into the tissue and detecting the light that is transmitted and scattered by the tissue. However, reflectance type sensors include an emitter 16 and detector 18 that are typically placed on the same side of the sensor site. For example, a reflectance type sensor may be placed on a patient's fingertip or forehead such that the emitter 16 and detector 18 lie side-by-side. Reflectance type sensors detect light photons that are scattered back to the detector 18. A sensor assembly 10 may also be a "transflectance" sensor, such as a sensor that may subtend a portion of a baby's heel.

While the disclosure may be susceptible to various modifications and alternative forms, specific embodiments have been shown by way of example in the drawings and have been described in detail herein. However, it should be understood that the embodiments provided herein are not intended to be limited to the particular forms disclosed. Indeed, the disclosed embodiments may not only be applied to measurements of blood oxygen saturation, but these techniques may also be utilized for the measurement and/or analysis of other blood constituents. For example, using the same, different, or additional wavelengths, the present techniques may be utilized for the measurement and/or analysis of carboxyhemoglobin, met-hemoglobin, total hemoglobin, fractional hemoglobin, intravascular dyes, and/or water content. Rather, the various embodiments may cover all modifications, equivalents, and alternatives falling within the spirit and scope of the disclosure as defined by the following appended claims

What is claimed is:

1. An apparatus comprising:
   a stocking cap configured to be applied to a patient's head;
   a substrate disposed adjacent the stocking cap;
   a light emitter disposed on the substrate;
   a light detector disposed on the substrate;
   a cable disposed on the substrate, wherein the cable extends from the substrate through an open portion of the stocking cap configured to be proximate to a top of the stocking cap when the stocking cap is applied to the patient; and
   a compressible protrusion disposed on the substrate, wherein the compressible protrusion is configured to substantially surround at least one of the emitter or the detector, and wherein the compressible protrusion is compressed to less than about 50% of its uncompressed height when the stocking cap is applied to the patient's head.

2. The apparatus of claim 1, wherein the compressible protrusion protrudes at least about 1 mm from the substrate.

3. The apparatus of claim 1, wherein the compressible protrusion protrudes substantially orthogonally from the substrate.

4. The sensor, as set forth in claim 1, comprising a second compressible protrusion that substantially surrounds the detector.

5. The sensor, as set forth in claim 1, wherein the compressible protrusion comprises a light reflecting material on a first surface and a light absorbing material on a second surface.

6. The sensor, as set forth in claim 5, wherein the first surface faces the emitter and the second surface opposes the emitter.

7. The sensor, as set forth in claim 1, wherein the compressible protrusion comprises a foam or gel.

8. The sensor, as set forth in claim 1, wherein the compressible protrusion is disposed on less than 10% of a surface of the substrate.

9. The apparatus of claim 1, wherein the stocking cap comprises a stocking cap configured to be placed on the head of a neonate.

10. The apparatus of claim 1, wherein the stocking cap is configured to apply a pressure less than about 35 mm Hg to the patient's head.

11. The apparatus of claim 1, the compressible protrusion is compressed to a height of less than 2.5 mm when the stocking cap is applied to the patient's head.

12. A pulse oximetry system comprising:
    a pulse oximetry monitor; and
    a sensor assembly configured to be operatively coupled to the monitor, the sensor assembly comprising:
    a light emitter and a light detector disposed on a substrate;
    a compressible protrusion disposed on the substrate in an area between the emitter and the detector, wherein the compressible protrusion does not substantially exsanguinate the patient's tissue when the sensor is assembly is applied to a patient's tissue, and wherein the compressible protrusion has a compression modulus of less than about 2.0; and
    a cable disposed on the substrate, wherein the cable is configured to be coupled to the monitor.

13. The system, as set forth in claim 12, wherein the sensor assembly comprises a headband.

14. The system, as set forth in claim 12, wherein the compressible protrusion is configured to be compressed substantially flush with the tissue at an applied pressure of greater than 35 mm Hg.

15. The system, as set forth in claim 12, wherein the compressible protrusion is configured to be compressed substantially flush with the tissue at an applied pressure of greater than about 80 mm Hg.

16. The system, as set forth in claim 12, wherein the compressible protrusion is compressed to about 50% of its uncompressed height when the substrate is applied to the tissue.

17. The system, as set forth in claim 12, wherein the compressible protrusion is compressed to a height of less than 2.5 mm when the substrate is applied to the tissue.

18. A sensor comprising:
   a cap configured to be applied to a patient's head;
   a sensor body disposed on the cap, and adapted to operate in a reflectance mode;
   an emitter disposed on the sensor body, wherein the emitter is configured to deliver a first light into a tissue;
   a detector disposed on the sensor body, wherein the detector is configured to detect the first light; and
   a compressible protrusion disposed on a tissue-contacting surface of the substrate, wherein the compressible protrusion is configured to reduce the amount of a second light impinging the detector at an incident angle substantially in-line with an imaginary axis connecting the emitter and the detector, and wherein the compressible protrusion has a compression modulus of less than about 2.0.

19. The sensor of claim 18, wherein the sensor comprises at least one of a pulse oximetry sensor or a sensor for measuring a water fraction.

20. The sensor of claim 18, wherein the compressible protrusion is disposed in a region between the emitter and the detector.

21. The sensor of claim 18, wherein the compressible protrusion comprises, silicone, polyvinylchloride, a foam or a gel.

22. The sensor of claim 18, wherein the compressible protrusion is configured to be compressed to 25% of its uncompressed height when the sensor is applied to a patient.

23. The sensor of claim 18, wherein the compressible protrusion is compressed from an uncompressed height greater than 5 mm to a compressed height of less than 2.5 mm when the sensor is applied to a patient.

24. The sensor of claim 18, wherein the compressible protrusion is compressed from an uncompressed height greater than 2 mm to a compressed height of less than 1 mm when the sensor is applied to a patient.

* * * * *